(12) United States Patent
Chaturvedula et al.

(10) Patent No.: US 7,449,586 B2
(45) Date of Patent: Nov. 11, 2008

(54) PROCESSES FOR THE PREPARATION OF CGRP-RECEPTOR ANTAGONISTS AND INTERMEDIATES THEREOF

(75) Inventors: Prasad V. Chaturvedula, Cheshire, CT (US); Xiaojan Han, Cheshire, CT (US); Xiang-Jun J. Jiang, North Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 540 days.

(21) Appl. No.: 11/291,670

(22) Filed: Dec. 1, 2005

(65) Prior Publication Data

US 2006/0122250 A1 Jun. 8, 2006

Related U.S. Application Data

(60) Provisional application No. 60/633,159, filed on Dec. 3, 2004.

(51) Int. Cl.
C07D 231/56 (2006.01)
(52) U.S. Cl. .............. 548/362.5; 548/356.1; 548/358.1; 548/360.1; 548/361.1
(58) Field of Classification Search .............. 548/356.1, 548/358.1, 360.1, 361.1, 362.5
See application file for complete search history.

(56) References Cited

U.S. PATENT DOCUMENTS

| | | | |
|---|---|---|---|
| 6,313,097 B1 | 11/2001 | Eberlein et al. |
| 6,344,449 B1 | 2/2002 | Rudolf et al. |
| 6,521,609 B1 | 2/2003 | Doods et al. |
| 6,552,043 B1 | 4/2003 | Patchett et al. |
| 2001/0036946 A1 | 11/2001 | Rudolf et al. |
| 2003/0139417 A1 | 7/2003 | Eberlein et al. |
| 2003/0181462 A1 | 9/2003 | Doods et al. |
| 2003/0191068 A1 | 10/2003 | Trunk et al. |
| 2003/0212057 A1 | 11/2003 | Rudolf et al. |
| 2003/0236282 A1 | 12/2003 | Hurnaus et al. |
| 2004/0014679 A1 | 1/2004 | Trunk et al. |
| 2004/0063735 A1 | 4/2004 | Chaturvedula et al. |
| 2004/0076587 A1 | 4/2004 | Kruss et al. |
| 2004/0132716 A1 | 7/2004 | Rudolf et al. |
| 2004/0192729 A1 | 9/2004 | Rudolf et al. |
| 2004/0204397 A1 | 10/2004 | Chaturvedula et al. |
| 2004/0214819 A1 | 10/2004 | Rudolf et al. |
| 2004/0229861 A1 | 11/2004 | Burgey et al. |
| 2004/0248816 A1 | 12/2004 | Doods et al. |
| 2005/0032783 A1 | 2/2005 | Doods et al. |
| 2005/0065094 A1 | 3/2005 | Davidai |
| 2005/0153959 A1 | 7/2005 | Luo et al. |
| 2005/0192230 A1 | 9/2005 | Linz et al. |
| 2005/0215546 A1 | 9/2005 | Hurnaus et al. |
| 2005/0215576 A1 | 9/2005 | Degnan et al. |
| 2005/0227968 A1 | 10/2005 | Lustenberger et al.. |
| 2005/0233980 A1 | 10/2005 | Doods et al. |
| 2005/0234054 A1 | 10/2005 | Mueller et al. |
| 2005/0234067 A1 | 10/2005 | Mueller et al. |
| 2005/0250763 A1 | 11/2005 | Mueller et al. |
| 2005/0256098 A1 | 11/2005 | Burgey et al. |
| 2005/0256099 A1 | 11/2005 | Mueller et al. |
| 2005/0272955 A1 | 12/2005 | Zimmer et al. |
| 2006/0094707 A1 | 5/2006 | Chaturvedula et al. |

FOREIGN PATENT DOCUMENTS

| | | |
|---|---|---|
| CA | 2 387 613 | 5/2001 |
| CA | 2 503 455 | 4/2005 |
| EP | 1 227 090 A1 | 7/2002 |
| WO | WO 97/09046 | 3/1997 |
| WO | WO 98/09630 | 3/1998 |
| WO | WO 98/11128 | 3/1998 |
| WO | WO 98/56779 | 12/1998 |
| WO | WO 99/52875 | 10/1999 |
| WO | WO 00/18764 | 4/2000 |
| WO | WO 00/55154 | 9/2000 |
| WO | WO 01/32648 | 3/2001 |
| WO | WO 01/25228 | 4/2001 |
| WO | WO 01/32649 | 5/2001 |
| WO | WO 01/49676 | 7/2001 |
| WO | WO 02/10140 | 2/2002 |
| WO | WO 03/027252 | 4/2003 |
| WO | WO 03/070753 | 8/2003 |
| WO | WO 03/076432 | 9/2003 |
| WO | WO 03/104236 | 12/2003 |
| WO | WO 2004/037810 | 5/2004 |
| WO | WO 2004/082602 A2 | 9/2004 |
| WO | WO 2004/082605 A2 | 9/2004 |
| WO | WO 2004/082678 A1 | 9/2004 |
| WO | WO 2004/083187 A1 | 9/2004 |
| WO | WO 2004/087649 A2 | 10/2004 |
| WO | WO 2004/091514 A2 | 10/2004 |
| WO | WO 2004/092166 A2 | 10/2004 |
| WO | WO 2004/092168 A1 | 10/2004 |
| WO | WO 2005/000807 | 1/2005 |
| WO | WO 2005/009962 | 2/2005 |
| WO | WO 2005/013894 | 2/2005 |
| WO | WO 2005/056550 | 6/2005 |
| WO | WO 2005/065779 | 7/2005 |
| WO | WO 2005/072308 | 8/2005 |
| WO | WO2005/084672 | 9/2005 |
| WO | WO 2005/092880 | 10/2005 |
| WO | WO 2005/095383 | 10/2005 |
| WO | WO/2005/100343 | 10/2005 |
| WO | WO/2005/100352 | 10/2005 |

(Continued)

OTHER PUBLICATIONS

U.S. Appl. No. 11/247,697, dated Oct. 11, 2005, Chaturvedula et al.

(Continued)

*Primary Examiner*—Golam M Shameem
(74) *Attorney, Agent, or Firm*—James Epperson

(57) ABSTRACT

The invention relates to novel processes for the preparation of small molecule antagonists of calcitonin gene-related peptide receptors ("CGRP-receptor") and intermediates thereof.

1 Claim, No Drawings

FOREIGN PATENT DOCUMENTS

| WO | WO/2005/100360 | 10/2005 |
| --- | --- | --- |
| WO | WO 2005/102322 | 11/2005 |
| WO | WO 2005/103037 | 11/2005 |
| WO | WO/2005/121078 | 12/2005 |
| WO | WO2006/052378 | 5/2006 |
| WO | WO 2006/060678 | 6/2006 |

OTHER PUBLICATIONS

Ashina, M., et al., "Evidence for increased plasma levels of calcitonin gene-related peptide in migraine outside of attacks", *Pain*, 2000, 86(1-2):133-138.

Brain, S.D., et al., "CGRP receptors: a headache to study, but will antagonists prove therapeutic in migraine?", *TiPS*, 2002, 23(2): 51-53.

Carlström, A.-S. and Frejd, T., Palladium-Catalyzed Synthesis of Didehydroamino Acid Derivatives, *Synthesis*, 1989, 6, 414-418.

Carlström, A.-S. and Frejd, T., "Palladium-Catalyzed Bis-coupling of Dihaloaromatics with 2-Amidoacrylates", *J. Org. Chem.*, 1991, 56: 1289-1293.

Chu, D.Q., et al., "The calcitonin gene-related peptide (CGRP) antagonist CGRP8-37 blocks vasodilatation in inflamed rat skin: involvement of adrenomedullin in addition to CGRP," *Neuroscience Letters*, 2001, 310:169-172.

De Vries, P., et al., "Pharmacological aspects of experimental headache models in relation to acute antimigraine therapy," *European Journal of Pharmacology*, 1999, 375: 61-74.

Doods, H., et al., "Pharmacological profile of BIBN4096BS, the first selective small molecule CGRP antagonist," *British Journal of Pharmacology*, 2000, 129: 420-423.

Dygos, J.H., "A Convenient Asymmetric Synthesis of the Unnatural Amino Acid 2,6-Dimethyl-L-tyrosine", *Synthesis*, 1992, 741-743.

Edvinsson, L., "Calcitonin Gene-Related Peptide (CGRP) and the Pathophysiology of Headache", *CNS Drugs*, 2001, 15 (10):745-753.

Escott, K.J., et al., "Trigeminal ganglion stimulation increases facial skin blood flow in the rat: a major role for calcitonic gene-related peptide", *Brain Research*, 1995, 669: 93-99.

Escott, K.J., et al., "Effect of a calcitonin gene-related peptide antagonist (CGRP8-37) on skin vasodilatation and oedema induced by stimulation of the rat saphenous nerve", *British Journal of Pharmacology*, 1993, 110, 772-776.

Evans, B.N. et al., "CGRP-RCP, a Novel Protein Required for Signal Transduction at Calcitonin Gene-related Peptide and Adrenomedullin Receptors", *J. Biol. Chem.*, 2000, 275(4): 31438-31443.

Gallai, V., et al. "Vasoactive peptide levels in the plasma of young migraine patients with and without aura assessed both interictally and ictally", *Cephalalgia*, 1995;15: 384-390.

Goadsby, P.J., et al., "Vasoactive peptide release in the extracerebral circulation of humans during migraine headache", *Annals of Neurology*, 1990, 28(2):183-187.

Grant, A.D., "Evidence of a role for NK1 and CGRP receptors in mediating neurogenic vasodilatation in the mouse ear", *British Journal of Pharmacology*, 2002, 135: 356-362.

Hall, J.M. and Brain, S.D., "Interaction of amylin with calcitonin gene-related peptide receptors in the microvasculature of the hamster cheek pouch in vivo," *British Journal of Pharmacology*, 1999, 126: 280-284.

Hall, J.M., et al., "Interaction of human adrenomedullin 13-52 with calcitonin gene-related peptide receptors in the microvasculature of the rat and hamster," *British Journal of Pharmacology*, 1995, 114: 592-597.

Juaneda, C. et al. "The molecular pharmacology of CGRP and related peptide receptor subtypes", *TiPS*, 2000, 21: 432-438.

Lassen, L.H. et al. "CGRP may play a causative role in migraine", *Cephalalgia*, 2002, 22(1): 54-61.

Mallee, J.J., et al. "Receptor Activity-modifying Protein 1 Determines the Species Selectivity of Non-peptide CGRP Receptor Antagonist", *J. Biol. Chem.*, 2002, 277(16): 14294-14298.

McLatchie, L.M. et al., "RAMPs regulate the transport and ligand specificity of the calcitonin-receptor-like receptor", *Nature*, 1998, 393: 333-339.

Olesen, J. et al. "Calcitonin Gene-Related Peptide Receptor Antagonist BIBN 4096 BS for the Acute Treatment of Migraine", *New England J. of Medicine*, 2004, 350 (11): 1104-1110.

Pasternak, A., et al., "Potent, orally bioavailable somatostatin agonists: good absorption achieved by urea backbone cyclization", *Bioorganic & Medicinal Chemistry Letters*, Oxford GB, vol. 9, No. 3, Feb. 8, 1999, p. 491-496.

Poyner, D.R. et al., "Pharmacological characterization of a receptor for calcitonin gene-related peptide on rat, L6 myocytes", *British Journal of Pharmacology*, 1992, 105: 441-447.

Rosenfeld, M.G., et al., "Production of a novel neuropeptide encoded by the calcitonin gene via tissue-specific RNA processing", *Nature*, 1983, 304:129-135.

Rudolf, K., et al., "Development of Human Calcitonin Gene-Related Peptide (CGRP) Receptor Antagonists. 1. Potent and Selective Small Molecule CGRP Antagonists. 1-[$N^2$-[3,5-Dibromo-$N$-[[4-(3,4-dihydro-2(1$H$)-oxoquinazolin-3-yl)-1-piperidinyl]carbonyl]-D-tyrosyl] L-lysyl]-4-(4-pyridinyl)piperazine: The First CGRP Antagonist for Clinical Trials in Acute Migraine", *J. Med. Chem.* 2005, 48: 5921-5931.

Shen, Y-T. et al., "Functional Role of α-Calcitonin Gene-Related Peptide in the Regulation of the Cardiovascular System", *J. Pharm. Exp. Ther.*, 2001, 298: 551-558.

Van Valen, F. et al., "Calcitonin gene-related peptide(CGRP) receptors are linked to cyclic adenosine monophosphate production in SK-N-MC human neuroblastoma cells", *Neuroscience Letters*, 1990, 119: 195-198.

Williamson, D.J. and Hargreaves, R.J., "Neurogenic Inflammation in the Context of Migraine", *Microsc. Res. Tech.*, 2001, 53: 167-178.

Williamson, D.J., et al., "Intravital microscope studies on the effects of neurokinin agonists and calcitonin gene-related peptide on dural vessel diameter in the anaesthetized rat," *Cephalalgia*, 1997, 17:518-524.

Williamson, D.J., et al., "Sumatriptan inhibits neurogenic vasodilation of dural blood vessels in the anaesthetized rat-intravital microscope studies," *Cephalalgia*, 1997, 17: 525-531.

Xin, Z., et al., "Potent, Selective Inhibitors of Protein Tyrosine Phosphatase IB", *Bioorg. Med. Chem. Lett.*, 2003, 13: 1887-1890.

U.S. Appl. No. 11/417,326, filed May 3, 2006, Chaturvedula et al.

PROCESSES FOR THE PREPARATION OF CGRP-RECEPTOR ANTAGONISTS AND INTERMEDIATES THEREOF

CROSS-REFERENCE TO RELATED APPLICATIONS

This is a non-provisional application which claims the benefit of U.S. Provisional Application No. 60/633,159 filed Dec. 3, 2004.

FIELD OF THE INVENTION

The present invention relates to novel small molecule antagonists of calcitonin gene-related peptide receptors ("CGRP-receptor"), pharmaceutical compositions comprising them, methods for preparing them, methods for identifying them, methods of treatment using them and their use in therapy for treatment of neurogenic vasodilation, neurogenic inflammation, migraine, cluster headache and other headaches, thermal injury, circulatory shock, flushing associated with menopause, airway inflammatory diseases, such as asthma and chronic obstructive pulmonary disease (COPD), and other conditions the treatment of which can be effected by the antagonism of CGRP-receptors.

BACKGROUND OF THE INVENTION

Calcitonin gene-related peptide (CGRP) is a naturally occurring 37-amino-acid peptide first identified in 1982 (Amara, S. G. et al, *Science* 1982, 298, 240-244). Two forms of the peptide are expressed (αCGRP and βCGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, *Br J Pharmacol* 1992, 105, 441-7; Van Valen, F. et al, *Neurosci Lett* 1990, 119, 195-8). Two classes of CGRP receptors, $CGRP_1$ and $CGRP_2$, have been proposed based on the antagonist properties of the peptide fragment CGRP(8-37) and the ability of linear analogues of CGRP to activate $CGRP_2$ receptors (Juaneda, C. et al. *TiPS* 2000, 21, 432-438). However, there is lack of molecular evidence for the $CGRP_2$ receptor (Brain, S. D. et al, *TiPS* 2002, 23, 51-53). The $CGRP_1$ receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al., *J Biol Chem.* 2000, 275, 31438-43). RAMP1 is required for transport of CRLR to the plasma membrane and for ligand binding to the CGRP-receptor (McLatchie, L. M. et al, *Nature* 1998, 393, 333-339). RCP is required for signal transduction (Evans B. N. et al., *J Biol Chem.* 2000, 275, 31438-43). There are known species-specific differences in binding of small molecule antagonists to the CGRP-receptor with typically greater affinity seen for antagonism of the human receptor than for other species (Brain, S. D. et al, *TiPS* 2002, 23, 51-53). The amino acid sequence of RAMP1 determines the species selectivity, in particular, the amino acid residue Trp74 is responsible for the phenotype of the human receptor (Mallee et al. *J Biol Chem* 2002, 277, 14294-8).

Inhibitors at the receptor level to CGRP are postulated to be useful in pathophysiologic conditions where excessive CGRP receptor activation has occurred. Some of these include neurogenic, vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. *CNS Drugs* 2001; 15(10): 745-53; Williamson, D. J. *Microsc. Res. Tech.* 2001, 53, 167-178; Grant, A. D. *Brit. J. Pharmacol.* 2002, 135, 356-362). Serum levels of CGRP are elevated during migraine (Goadsby P J, et al. *Ann Neurol* 1990; 28:183-7) and treatment with anti-migraine drugs returns CGRP levels to normal coincident with alleviation of headache (Gallai V. et al. *Cephalalgia* 1995; 15: 384-90). Migraineurs exhibit elevated basal CGRP levels compared to controls (Ashina M, et al., Pain. 2000; 86(1-2):133-8.2000). Intravenous CGRP infusion produces lasting headache in migraineurs (Lassen L H, et al. *Cephalalgia.* 2002 February; 22(1):54-61). Preclinical studies in dog and rat report that systemic CGRP blockade with the peptide antagonist CGRP(8-37) does not alter resting systemic hemodynamics nor regional blood flow (Shen, Y-T. et al, *J Pharmacol Exp Ther* 2001, 298, 551-8). Thus, CGRP-receptor antagonists may present a novel treatment for migraine that avoids the cardiovascular liabilities of active vasoconstriction associated with non-selective $5-HT_{1B/1D}$ agonists, 'triptans' (e.g., sumatriptan).

A number of non-peptidic, small molecule CGRP-receptor antagonists have been recently reported. WO 97/09046 and equivalents disclose inter alia quinine and quinidine related compounds which are ligands, in particular antagonists, of CGRP-receptor. WO 98/09630 and WO 98/56779 and equivalents disclose inter alia variously substituted, nitrobenzamide compounds as CGRP-receptor antagonists. WO 01/32649, WO 01/49676, and WO 01/32648 and equivalents disclose inter alia a series of 4-oxobutanamides and related cyclopropane derivatives as CGRP-receptor antagonists. WO 00/18764, WO 98/11128 and WO 00/55154 and equivalents disclose inter alia benzimidazolinyl piperidines as antagonists to CGRP-receptor. Unrelated to CGRP, a series of somatostatin antagonists have been disclosed in WO 99/52875 and WO 01/25228 and equivalents. See also U.S. Pat. Nos. 6,344, 449, 6,313,097, 6,521,609, 6,552,043, US 20030181462, US20030191068 and WO 03/076432 and related applications. Yet other CGRP-receptor antagonist and related applications include US20030139417A1, US20030181462, US20030191068A1, US20030212057A1, US20030236282A1, US20040014679A1, US20040076587A1, US20040132716A1, US20040192729A1, WO2004082602A2, WO2004082605A2, WO2004082678A1, WO2004083187A1, WO2004092168A1, WO2004092166A2 and WO2004091514A2.

Efficient processes for synthesizing CGRP-receptor antagonists and their intermediates are greatly desirable. Present syntheses of these intermediates often rely on the addition and removal of protecting groups for the amino acid side chain. These synthetic manipulations add cost and length to manufacturing processes and inevitably reduce overall yields of target compounds. Alternative syntheses of these amino acids which do not require protection and deprotection of side chain functional groups would allow CGRP antagonists to be prepared more efficiently and more particularly for large scale operations. Thus, the present invention provides inter alia novel processes (incorporating Heck reactions) and intermediates useful in the synthesis of CGRP-receptor antagonists. See Syntheses of amino acids using the Heck reaction have been disclosed. See Xin, Z. et al. *Bioorg. Med. Chem. Lett.* 2003, 13, 1887; Dygos, J. H. et al. *Synthesis* 1992, 8, 741; Carlstrom, A.-J. and Frejd, T. *J. Org. Chem.* 1991, 56, 1289; Carlstrom, A.-J. and Frejd, T. *Synthesis* 1989, 6, 414.

SUMMARY OF THE INVENTION

Thus according to a first embodiment of a first aspect of the invention is a process for synthesizing a compound of Formula (Ia)

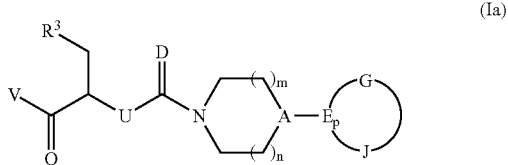

or a pharmaceutically acceptable salt or solvate thereof
wherein
V is —N($R^1$)($R^2$) or $OR^4$;
$R^{4'}$ is $C_{3-7}$cycloalkyl, phenyl, adamantyl, quinuclidyl, azabicyclo[2.2.1]heptyl, azetidinyl, tetrahydrofuranyl, furanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino or dioxolanyl; and $R^{4'}$ is optionally substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, ($C_{1-3}$alkyl)$_{0-2}$ureido, phenyl and benzyl; and $R^{4'}$ optionally contains 1 or 2 carbonyls wherein the carbon atom of said carbonyl is a member of the ring structure of $R^{4'}$;

$R^1$ and $R^2$ are each independently $L^1$, wherein $L^1$ is selected from the group consisting of H, $C_{1-6}$alkyl, $C_{2-6}$alkenyl, $C_{2-6}$alkynyl, —$C_{1-6}$alkylene-amino($C_{1-3}$alkyl)$_2$, $C_{3-7}$cycloalkyl, phenyl, azetidinyl, adamantyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and $R^1$ and $R^2$ are each optionally and independently substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, ($C_{1-3}$alkyl)$_{0-2}$ureido, phenyl and benzyl;

$R^1$ and $R^2$ optionally and independently contain 1 or 2 carbonyls wherein the carbon atom of said carbonyl is a member of the heterocycles comprising $R^1$ and $R^2$;

wherein $L^1$ is optionally and independently interrupted from the nitrogen to which it is attached by $L^2$, wherein $L^2$ is independently $C_{1-3}$alkylene or $C_{1-3}$alkylidene; or $R^1$ and $R^2$ together with the nitrogen to which they are attached form X, wherein X is azetidinyl, pyrrolyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or thiomorpholino;

wherein X is optionally substituted with Y, wherein Y is dioxolanyl, $C_{1-9}$alkyl, $C_{2-9}$alkenyl, $C_{2-9}$alkynyl, $C_{1-4}$alkylamino, $C_{1-4}$dialkylamino, $C_{1-4}$alkoxy, $C_{3-7}$cycloalkyl, phenyl, azetidinyl, furanyl, thienyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino;

and wherein X and Y are optionally interrupted with Z, wherein Z is —NHC(O)O—, —NHC(O)NH—, NC(O)NH$_2$, —NH—, —$C_{1-3}$alkenylene-, —$C_{1-3}$alkenylene-NHC(O)O—$C_{1-3}$alkenylene-; and optionally and independently substituted with 1 or 2 of the same or different substituents selected from the group consisting of $C_{1-4}$alkyl, amino, $C_{1-3}$alkylamino, —$C_{1-4}$alkylene-amino($C_{1-3}$alkyl)$_2$, ($C_{1-3}$alkyl)$_{0-2}$ureido, phenyl and benzyl;

X and Y optionally and independently contain 1 or 2 carbonyls wherein the carbon atom of said carbonyl is a member of the heterocycles comprising X and Y;

provided that if X is substituted with Y, and if X and Y are not interrupted with Z, then X and Y optionally share one carbon atom and together form a spirocyclic moiety;

U is NH;

$R^3$ is (i) a heteroaryl having two fused rings with 5 to 7 members in each of said rings, said heteroaryl containing one to five of the same or different heteroatoms selected from the group consisting of O, N and S and said heteroaryl optionally containing 1 or 2 carbonyls wherein the carbon atom of said carbonyl is a member of said fused rings;

(ii) a 5 to 6 membered heteroaryl containing one to three of the same or different heteroatoms selected from the group consisting of O, N and S, optionally containing 1 to 2 carbonyls, wherein the carbon atom of said carbonyl is a member of said 5 to 6 membered heteroaryl;

(iii) phenyl, fluorenyl or napthyl;

wherein $R^3$ is optionally substituted with 1 to 3 of the same or different substituents selected from the group consisting of benzyl, phenyl, —O-phenyl, —O-$C_{1-3}$alkylenephenyl, —$C_{1-3}$alkylene-OC(O)-phenyl, cyano, amino, nitro, halo, $C_{1-6}$alkyl, $C_{1-3}$mono-bi-tri-haloalkyl, $C_{1-3}$mono-bi-tri-haloalkyloxy, ($C_{1-3}$alkyl)$_{1-2}$amine, —$OR^{3'}$, —C(O)$R^{3'}$, —C(O)O—$R^{3'}$, —O—C(O)$R^{3'}$, —N(R$^{3'}$)$_2$, —C(O)N(R$^{3'}$)$_2$, —N(R$^{3'}$)C(O)(R$^{3'}$)$_2$, —N(R$^{3'}$)C(O)N(R$^{3'}$)$_2$, —N(R$^{3'}$)C(O)OR$^{3'}$, —O—C(O)N(R$^{3'}$)$_2$, —N(R$^{3'}$)SO$_2$R$^{3'}$, —SO$_2$N(R$^{3'}$)$_2$ and —SO$_2$R$^{3'}$;

R$^{3'}$ is H or —C$_{1-6}$alkyl;

provided that if R$^3$ is —C(O)R$^{3'}$, CHC(O)O—R$^{3'}$, CH(CH$_3$)C(O)O—R$^{3'}$ or —C(O)O—R$^{3'}$, then said —C(O)R$^{3'}$, CHC(O)O—R$^{3'}$, CH(CH$_3$)C(O)O—R$^{3'}$ or —C(O)O—R$^{3'}$ are unsubstituted;

D is O, NCN or NSO$_2$C$_{1-3}$alkyl;

A is C, N or CH;

m and n are independently 0, 1 or 2;

provided that
if m and n are 0, then A is not N;
if m is 2, then n is not 2; or
if n is 2, then m is not 2;

E is N, CH or C;

p is 0 or 1;

if p is 1, then G, J and E together form A$^x$ or A$^y$;
A$^x$ is a fused heterocycle having two fused rings with 5 to 7 members in each of said rings, said heterocycle containing one to four of the same or different heteroatoms selected from the group consisting of O, N and S; and
optionally containing 1 or 2 carbonyls wherein the carbon atom of said carbonyl is a member of said fused heterocycle;
A$^y$ is a 4 to 6 membered heterocycle containing one to three heteroatoms selected from the group consisting of O, N and S; and
optionally containing 1 to 2 carbonyls, wherein the carbon atom of said carbonyl is a member of said 4 to 6 membered heterocycle;
wherein A$^x$ and A$^y$ are optionally substituted with C$_4$alkyl, C$_{1-4}$alkoxy, C$_{1-4}$haloalkyl, cyano, C$_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino; or if p is 0 such that G and J are each attached to A, then A is C, and G, J and A together form a spirocyclic ring system with said rings of said system containing A and wherein G, J and A together are GJA' or GJA";
wherein
GJA' is A$^x$ or A$^y$; and
GJA" is A$^x$ or A$^y$;
provided that
A$^x$ is not a 1,3-diaza-fused heterocycle; and
A$^y$ is not a 1,3-diaza-heterocycle;

wherein said process comprises
(a) coupling a compound of Formula IX

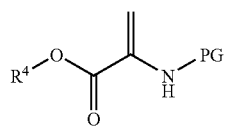

IX wherein
R$^4$ is C$_{1-6}$alkyl or benzyl; and
PG is BOC, CBZ, or FMOC with R$^3$X
wherein
R3 is as defined above; and
X is bromo, iodo or a sulfonate selected from the group consisting of mesylate, tosylate and triflate
to form a compound of Formula XI

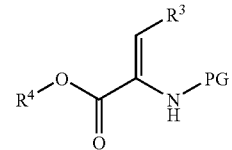

XI (b) reducing said compound of Formula XI to form a compound of Formula XII

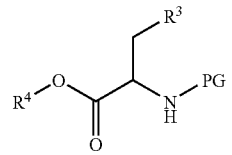

XII (c) hydrolyzing said compound of Formula XII to form a compound of Formula II or a salt thereof;

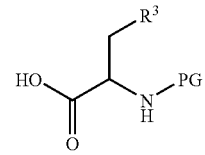

II (d) reacting said compound of Formula II with an amine of Formula HNR$^1$R$^2$ to form a compound of Formula III;

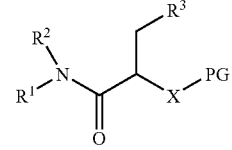

III (e) deprotecting said compound of Formula III to form a compound of Formula IV or a salt thereof; and

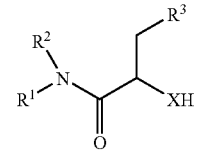

IV (f) reacting said compound of Formula IV with a compound of Formula V to form a compound of Formula Ia or a salt thereof.

According to a second embodiment of the first aspect of the invention is a process for synthesizing a compound of Formula Ia as defined in the first embodiment of the first aspect wherein said process comprises (a) coupling a compound of Formula IX wherein
$R^4$ is $C_{1-6}$alkyl or benzyl; and
PG is BOC, CBZ, or FMOC
with $R^3X$
wherein
R3 is as defined above; and
X is bromo, iodo or a sulfonate selected from the group consisting of mesylate, tosylate and triflate to form a compound of Formula XI;

(b) reducing said compound of Formula XI to form a compound of Formula XII;

(c) hydrolyzing said compound of Formula XII to form a compound of Formula VI or a salt thereof;

(d) reacting said compound of Formula VI with an amine of Formula V in a mixed urea or urea isostere reaction to form a compound of Formula VII;

(e) hydrolyzing said compound of Formula VII to form a compound of Formula VIII or a salt thereof, and (f) reacting said compound of Formula VIII with an amine of Formula $HNR^1R^2$ to form a compound of Formula Ia or a salt thereof.

According to a first embodiment of a second aspect of the invention is a process for synthesizing a compound of Formula (Ia)

or a pharmaceutically acceptable salt or solvate thereof
wherein
V is $-N(R^1)(R^2)$ or $OR^4$;
$R^4$ is H, $C_{1-6}$alkyl, $C_{1-4}$haloalkyl or $(C_{1-4}alkylene)_{0-1}R^{4'}$
$R^{4'}$ is $C_{3-7}$cycloalkyl, phenyl, adamantyl, quinuclidyl, azabicyclo[2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino or dioxolanyl; and
$R^{4'}$ is optionally substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, $(C_{1-3}$alkyl$)_{0-2}$ureido, phenyl and benzyl; and $R^{4'}$ optionally contains 1 or 2 carbonyls wherein the carbon atom of said carbonyl is a member of the ring structure of $R^{4'}$;

$R^1$ and $R^2$ are each independently $L^1$, wherein $L^1$ is selected from the group consisting of H, $C_{1-6}$alkyl, $C_{2-6}$alkenyl, $C_{2-6}$alkynyl, —$C_{1-6}$alkylene-amino($C_{1-3}$alkyl$)_2$, $C_{3-7}$cycloalkyl, phenyl, azetidinyl, adamantyl, tetrahydrofuranyl, furanyl, thienyl, tetrahydrothienyl, pyrrolyl, pyrrolinyl, pyrrolidinyl, imidazolyl, imidazolinyl, imidazolidinyl. pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and $R^1$ and $R^2$ are each optionally and independently substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, $(C_{1-3}$alkyl$)_{0-2}$ureido, phenyl and benzyl;

$R^1$ and $R^2$ optionally and independently contain 1 or 2 carbonyls wherein the carbon atom of said carbonyl is a member of the heterocycles comprising $R^1$ and $R^2$;

wherein $L^1$ is optionally and independently interrupted from the nitrogen to which it is attached by $L^2$, wherein $L^2$ is independently $C_{1-3}$alkylene or $C_{1-3}$alkylidene; or $R^1$ and $R^2$ together with the nitrogen to which they are attached form X, wherein X is azetidinyl, pyrrolyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or thiomorpholino;

wherein X is optionally substituted with Y, wherein Y is dioxolanyl, $C_{1-9}$alkyl, $C_{2-9}$alkenyl, $C_{2-9}$alkynyl, $C_{1-4}$alkylamino, $C_4$dialkylamino, $C_4$alkoxy, $C_{3-7}$cycloalkyl, phenyl, azetidinyl, furanyl, thienyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino;

and wherein X and Y are optionally interrupted wit Z, wherein Z is —NHC(O)O—, —NHC(O)NH—, NC(O)NH$_2$, —NH—, —$C_{1-3}$alkylene-, —$C_{1-3}$alkenylene-NHC(O)O—$C_{1-3}$alkylene-; and optionally and independently substituted with 1 or 2 of the same or different substituents selected from the group, consisting of $C_{1-4}$alkyl, amino, $C_{1-3}$alkylamino, —$C_{1-6}$alkylene-amino($C_{1-3}$alkyl$)_2$, $(C_{1-3}$alkyl$)_{0-2}$ureido, phenyl and benzyl;

X and Y optionally and independently contain 1 or 2 carbonyls wherein the carbon atom of said carbonyl is a member of the heterocycles comprising X and Y;

provided that if X is substituted with Y, and if X and Y are not interrupted with Z, then X and Y optionally share one carbon atom and together form a spirocyclic moiety;

U is O;

$R^3$ is (iii) a heteroaryl having two fused rings with 5 to 7 members in each of said rings, said heteroaryl containing one to five of the same or different heteroatoms selected from the group consisting of O, N and S and said heteroaryl optionally containing 1 or 2 carbonyls wherein the carbon atom of said carbonyl is a member of said fused rings;

(iv) a 5 to 6 membered heteroaryl containing one to three of the same or different heteroatoms selected from the group consisting of O, N and S, optionally containing 1 to 2 carbonyls, wherein the carbon atom of said carbonyl is a member of said 5 to 6 membered heteroaryl;

(iii) phenyl, fluorenyl or napthyl;

wherein $R^3$ is optionally substituted with 1 to 3 of the same or different substituents selected from the group consisting of benzyl, phenyl, —O-phenyl, —O—$C_{1-3}$alkylenephenyl, —$C_{1-3}$alkylene-OC(O)-phenyl, cyano, amino, nitro, halo, $C_{1-6}$alkyl, $C_{1-3}$mono-bi-tri-haloalkyl, $C_{1-3}$mono-bi-tri-haloalkyloxy, $(C_{1-3}$alkyl$)_{1-2}$amine, —OR$^{3'}$, —C(O)R$^{3'}$, —C(O)O—R$^{3'}$, —O—C(O)R$^{3'}$, —N(R$^{3'}$)$_2$, C(O)N(R$^{3'}$), —N(R$^{3'}$)C(O)(R$^{3'}$)$_2$, —N(R$^{3'}$)C(O)N(R$^{3'}$)$_2$, —N(R$^{3'}$)C(O)OR$^{3'}$, —O—C(O)N(R$^{3'}$)$_2$, —N(R$^{3'}$)SO$_2$R$^{3'}$, —SO$_2$N(R$^{3'}$)$_2$ and —SO$_2$R$^{3'}$;

$R^{3'}$ is H or —$C_{1-6}$alkyl;

provided that if $R^3$ is —C(O)R$^{3'}$, CHC(O)O—R$^{3'}$, CH(CH$_3$)C(O)O—R$^{3'}$ or —C(O)O—R$^{3'}$, then said —C(O)R$^{3'}$, CHC(O)O—R$^{3'}$, CH(CH$_3$)C(O)O—R$^{3'}$ or —C(O)O—R$^{3'}$ are unsubstituted;

D is O, NCN or NSO$_2$C$_{1-3}$alkyl;

A is C, N or CH;

m and n are independently 0, 1 or 2;

provided that if m and n are 0, then A is not N;

if m is 2, then n is not 2; or if n is 2, then m is not 2;

E is N, CH or C;

p is 0 or 1;

if p is 1, then G, J and E together form $A^x$ or $A^y$;

$A^x$ is a fused heterocycle having two fused rings with 5 to 7 members in each of said rings, said heterocycle containing one to four of the same or different heteroatoms selected from the group consisting of O, N and S; and optionally containing 1 or 2 carbonyls wherein the carbon atom of said carbonyl is a member of said fused heterocycle;

$A^y$ is a 4 to 6 membered heterocycle containing one to three heteroatoms selected from the group consisting of O, N and S; and optionally containing 1 to 2 carbonyls, wherein the carbon atom of said carbonyl is a member of said 4 to 6 membered heterocycle;

wherein $A^x$ and $A^y$ are optionally substituted with $C_{1-4}$alkyl, $C_{1-4}$alkoxy, $C_{1-4}$haloalkyl, cyano, $C_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino; or if p is 0 such that G and J are each attached to A, then A is C, and G, J and A together form a spirocyclic ring system with said rings of said system containing A and wherein G, J and A together are GJA' or GJA";
wherein
  GJA' is $A^x$ or $A^y$; and
  GJA" is $A^x$ or $A^y$;
  provided that
    $A^x$ is not a 1,3-diaza-fused heterocycle; and
    $A^y$ is not a 1,3-diaza-heterocycle;
wherein said process comprises
(a) coupling a compound of Formula IX

IX $$\underset{R^4\diagup O \diagdown \diagup \diagdown N(H)PG}{\parallel O}$$

wherein
  $R^4$ is $C_{1-6}$alkyl or benzyl; and
  PG is BOC, CBZ, or FMOC
with $R^3X$
  wherein
    R3 is as defined above; and
    X is bromo, iodo or a sulfonate selected from the group consisting of mesylate, tosylate and triflate
to form a compound of Formula XI

XI (b) hydrolyze said compound of Formula XI to form a compound of Formula XIII

XIII (c) reduce said compound of Formula XIII to form a compound of Formula XIV

XIV (d) protect said compound of Formula XIV to form a compound of Formula XV

XV (e) hydrolyze said compound of Formula XV to form a compound of Formula XVI or a salt thereof; and

XVI (f) reacting said compound of Formula XVI with an amine of Formula $NHR^1R^2$ to form a compound of Formula III

III (g) deprotecting said compound of Formula III to form a compound of Formula IV or a salt thereof; and

IV (h) reacting said compound of Formula IV with a compound of Formula V

V to form a compound of Formula Ia or a salt thereof.

According to a second embodiment of the second aspect of the invention is a process for synthesizing a compound of Formula Ia as defined above wherein said process comprises
(a) coupling a compound of Formula IX

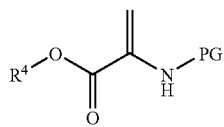

wherein
R⁴ is $C_{1-6}$alkyl or benzyl; and
PG is BOC, CBZ, or FMOC
with R³X
wherein
R3 is as defined above; and
X is bromo, iodo or a sulfonate selected from the group consisting of mesylate, tosylate and triflate
to form a compound of Formula XI;

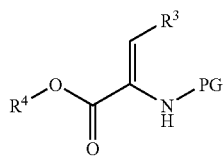

(b) hydrolyze said compound of Formula XI to form a compound of Formula XIII

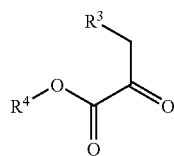

(c) reduce said compound of Formula XIII to form a compound of Formula XIV

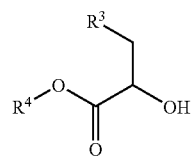

(d) react a compound of Formula XIV with a compound of Formula V in a mixed urea or urea isostere reaction to form a compound of Formula VII;

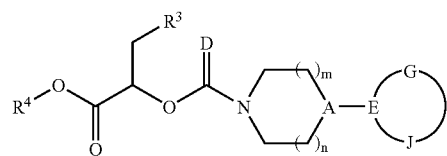

(e) hydrolyzing said compound of Formula VII to form a compound of Formula VIII or a salt thereof; and

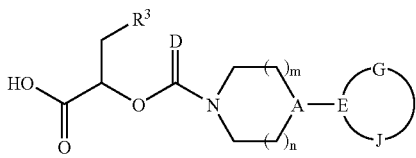

(f) reacting said compound of Formula VIII with an amine of Formula $HNR^1R^2$ to form a compound of Formula Ia or a salt thereof.

According to a first embodiment of a third aspect of the invention is a process for synthesizing a compound of Formula (Ib)

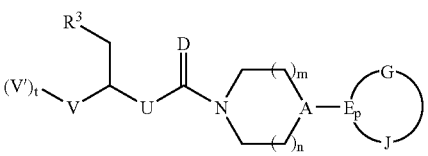

or a pharmaceutically acceptable salt or solvate thereof
wherein
V is
a 5-membered ring selected from the group consisting of imidazolyl, pyrazolyl, thiazolyl, isothiazolyl, oxazolyl, furanyl, isoxazolyl, oxadiazolyl, triazolyl, thiadiazolyl and tetrazolyl; or
a 6-membered ring selected from the group consisting of pyridyl, pyrimidinyl, triazinyl, pyrazinyl, pyridazinyl and tetrazinyl; or
a fused bicyclic ring system selected from the group consisting of indolyl, isoindolyl, indazolyl, benzimidazolyl, benzythiazolyl, triazolopyridinyl, imidazopyridinyl, quinolinyl, isoquinolinyl, cinnolinyl, phthalazinyl, quinazolinyl, quinoxalinyl and benzfuranyl;
wherein V is optionally substituted with one to three of the same or different substituents selected from the group consisting of $C_{1-4}$alkyl, $C_{1-4}$alkoxy, $C_{1-4}$hydroxyalkyl, $C(O)OC_{2-3}$alkyl, $C_{1-4}$alkylcarbonyl, carboxy, $C_{1-4}$alkylcarboxy, trifluoromethyl, halo, cyano, amino, amido, nitro, carbamoyl, ureido, $C_{1-4}$alkylamino, $C_{1-4}$dialkylamino, $C_{1-4}$dialkylamino$C_{1-2}$alkyl, sulphonamide and sulphonyl; and
V optionally contains 1 or 2 carbonyls; provided that if t is 1, then V is optionally substituted with one of
the substitutents selected from the group consisting of halo, $C_{1-4}$alkyl, $C_{1-4}$alkylidine, $C_{1-4}$alkoxy, $C_{1-4}$hydroxyalkyl, $C_{1-4}$alkylcarbonyl, trifluoromethyl, halo and cyano; and
V optionally contains 1 or 2 carbonyls;

(V')$_t$ wherein t is 0 or 1; and
V' is selected from the group consisting of C$_{3-7}$cycloalkyl, phenyl, adamantyl, quinuclidyl, azabicyclo[2.2.]heptyl, azetidinyl, tetrahydrofuranyl, furanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimildinyl, pyrazinyl, pyridazinyl, triazinyl, piperidinyl, piperazinyl, morpholino, thiomorpholino and dioxolanyl; and wherein
V' is optionally substituted with 1 or 2 of the same or different substituents selected from the group consisting of halo, cyano, C$_{1-4}$alkyl, C$_{1-4}$haloalkyl, C$_{1-4}$alkoxy, hydroxy, amino, C$_{3-7}$cycloalkyl, C$_{1-4}$alkylamino, C$_{1-4}$dialkylamino, (C$_{1-3}$alkyl)$_{0-2}$ureido, C(O)OC$_{2-3}$alkyl, carboxy, amido, nitro, phenyl and benzyl; and wherein
V' optionally contains 1 or 2 carbonyls; and
V and V' are optionally interrupted by C$_{1-3}$alkylene, O, —(CH$_2$)$_{0-2}$C(O)—(CH$_2$)$_{0-2}$—; or —N—C$_{1-4}$alkyl, said C$_{1-3}$alkylene being optionally interrupted by or having attached thereto O, N or S;
U is NH;
R$^3$ is
(i) a heteroaryl having two fused rings with 5 to 7 members in each of said rings, said heteroaryl containing one to five of the same or different heteroatoms selected from the group consisting of O, N and S and said heteroaryl optionally containing 1 or 2 carbonyls wherein the carbon atom of said carbonyl is a member of said fused rings;
(ii) a 5 to 6 membered heteroaryl containing one to three of the same or different heteroatoms selected from the group consisting of O, N and S, optionally containing 1 to 2 carbonyls, wherein the carbon atom of said carbonyl is a member of said 5 to 6 membered heteroaryl;
(iii) fluorenyl, phenyl or napthyl;
wherein R3 is optionally substituted with 1 to 3 of the same or different substituents selected from the group consisting of benzyl, phenyl, —O-phenyl, —O—C1-3alkylenephenyl, —C1-3alkylene-OC(O)-phenyl, cyano, amino, nitro, halo, C1-6alkyl, C1-3mono-bi-tri-haloalkyl, C1-3mono-bi-tri-haloalkyloxy, (C1-3alkyl) 1-2amine, —OR$^{3'}$, —C(O)R$^{3'}$, —C(O)O—R$^{3'}$, —O—C(O)R$^{3'}$, —N(R$^{3'}$)$_2$, —C(O)N(R$^{3'}$)$_2$, —N(R$^{3'}$)C(O)(R$^{3'}$)$_2$, —N(R$^{3'}$)C(O)N(R$^{3'}$)$_2$, —N(R$^{3'}$)C(O)OR$^{3'}$, —O—C(O)N(R$^{3'}$)$_2$, —N(R$^{3'}$)SO$_2$R$^{3'}$, —SO$_2$N(R$^{3'}$)$_2$ and —SO$_2$R$^{3'}$;
R$^{3'}$ is H or —C$_{1-6}$alkyl;
D is O, NCN or NSO$_2$C$_{1-3}$alkyl;
A is C, N or CH;
m and n are independently 0, 1 or 2;
provided that
if m and n are 0, then A is not N;
if m is 2, then n is not 2; or
if n is 2, thenmis not 2;
E is N, CH or C;
p is 0 or 1;
if p is 1, then G, J and E together form A$^x$ or A$^y$;
A$^x$ is a fused heterocycle having two fused rings with 5 to 7 members in each of said rings, said heterocycle containing one to four of the same or different heteroatoms selected from the group consisting of O, N and S; and
optionally containing 1 or 2 carbonyls wherein the carbon atom of said carbonyl is a member of said fused heterocycle;
A$^y$ is a 4 to 6 membered heterocycle containing one to three heteroatoms selected from the group consisting of O, N and S; and
optionally containing 1 to 2 carbonyls, wherein the carbon atom of said carbonyl is a member of said 4 to 6 membered heterocycle;
wherein A$^x$ and A$^y$ are optionally substituted with C$_{1-4}$alkyl, C$_{1-4}$alkoxy, C$_{1-4}$haloalkyl, cyano, C$_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino; or
if p is 0 such that G and J are each attached to A, then A is C, and G, J and A together form a spirocyclic ring system with said rings of said system containing A and wherein GJA is A$^x$ or A$^y$ wherein said process comprises
(a) coupling a compound of Formula IX

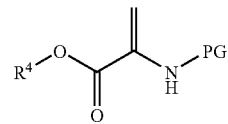

IX wherein
R$^4$ is C$_{1-6}$alkyl or benzyl; and
PG is BOC, CBZ, or FMOC
with R$^3$X
wherein
R3 is as defined above; and
X is bromo, iodo or a sulfonate selected from the group consisting of mesylate, tosylate and triflate
to form a compound of Formula XI;

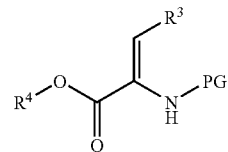

XI (b) reducing said compound of Formula XI to form a compound of Formula XII;

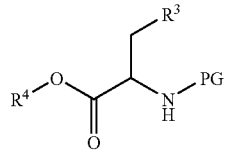

XII (c) hydrolyzing said compound of Formula XII to form a compound of Formula VI or a or a salt thereof;

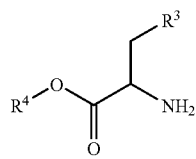

(d) reacting said compound of Formula VI with an amine of Formula V as defined above in a mixed urea or urea isostere reaction to form a compound of Formula VII;

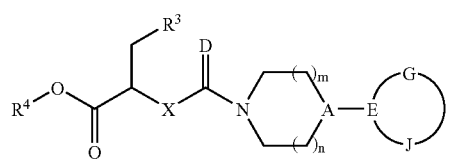

(e) hydrolyzing said compound of Formula VII to form a compound of Formula VIII or a salt thereof; and

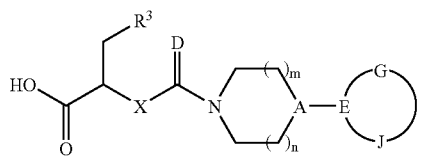

(f) transforming the carboxylic acid moiety of said compound of Formula VIII to $(V')_t V$ to form a compound of Formula Ib or a salt thereof.

According to a first embodiment of a fourth aspect of the invention is a process for synthesizing a compound of Formula (Ib)

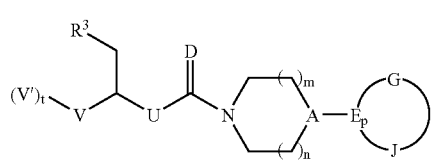

or a pharmaceutically acceptable salt or solvate thereof
wherein
V is
  a 5-membered ring selected from the group consisting of imidazolyl, pyrazolyl, thiazolyl, isothiazolyl, oxazolyl, furanyl,
  isoxazolyl, oxadiazolyl, triazolyl, thiadiazolyl and tetrazolyl; or
  a 6-membered ring selected from the group consisting of pyridyl, pyrimidinyl, triazinyl, pyrazinyl, pyridazinyl and tetrazinyl; or
  a fused bicyclic ring system selected from the group consisting of indolyl, isoindolyl, indazolyl, benzimidazolyl, benzythiazolyl, triazolopyridinyl, imidazopyridinyl, quinolinyl, isoquinolinyl, cinnolinyl, phthalazinyl, quinazolinyl, quinoxalinyl and benzfuranyl;

wherein V is optionally substituted with one to three of the same or different substituents selected from the group consisting of $C_{1-4}$alkyl, $C_{1-4}$alkoxy, $C_{1-4}$hydroxyalkyl, $C(O)OC_{2-3}$alkyl, $C_{1-4}$alkylcarbonyl, carboxy, $C_{1-4}$alkylcarboxy, trifluoromethyl, halo, cyano, amino, amido, nitro, carbamoyl, ureido, $C_{1-4}$alkylamino, $C_{1-4}$dialkylamino, $C_{1-4}$dialkylamino$C_{1-2}$alkyl, sulphonamide and sulphonyl; and V optionally contains 1 or 2 carbonyls; provided that if t is 1, then V is optionally substituted with one of the substitutents selected from the group consisting of halo, $C_{1-4}$alkyl, $C_{1-4}$alkylidine, $C_{1-4}$alkoxy, $C_{1-4}$hydroxyalkyl, $C_{1-4}$alkylcarbonyl, trifluoromethyl, halo and cyano; and V optionally contains 1 or 2 carbonyls;

$(V')_t$ wherein t is 0 or 1; and

V' is selected from the group consisting of $C_{3-7}$cycloalkyl, phenyl, adamantyl, quinuclidyl, azabicyclo[2.2.]heptyl, azetidinyl, tetrahydrofuranyl, furanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and wherein V' is optionally substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-4}$alkylamino, $C_{1-4}$dialkylamino, $(C_{1-3}$alkyl$)_{0-2}$ureido, $C(O)OC_{2-3}$alkyl, carboxy, amido, nitro, phenyl and benzyl; and wherein V' optionally contains 1 or 2 carbonyls; and V and V' are optionally interrupted by $C_{1-3}$alkylene, O, —$(CH_2)_{0-2}C(O)$—$(CH_2)_{0-2}$—; or —N—$C_{1-4}$alkyl, said $C_{1-3}$alkylene being optionally interrupted by or having attached thereto O, N or S;

U is O;

$R^3$ is (i) a heteroaryl having two fused rings with 5 to 7 members in each of said rings, said heteroaryl containing one to five of the same or different heteroatoms selected from the group consisting of O, N and S and said heteroaryl optionally containing 1 or 2 carbonyls wherein the carbon atom of said carbonyl is a member of said fused rings;

(ii) a 5 to 6 membered heteroaryl containing one to three of the same or different heteroatoms selected from the group consisting of O, N and S, optionally containing 1 to 2 carbonyls, wherein the carbon atom of said carbonyl is a member of said 5 to 6 membered heteroaryl;

(iii) fluorenyl, phenyl or napthyl;

wherein $R^3$ is optionally substituted with 1 to 3 of the same or different substituents selected from the group consisting of benzyl, phenyl, —O-phenyl, —O—$C_{1-3}$alkylenephenyl, —$C_{1-3}$alkylene-OC(O)-phenyl, cyano, amino, nitro, halo, $C_{1-6}$-alkyl, $C_{1-3}$mono-bi-tri-haloalkyl, $C_{1-3}$mono-bi-tri-haloalkyloxy, $(C_{1-3}alkyl)_{1-2}$amine, —OR$^{3'}$, —C(O)R$^{3'}$, —C(O)O—R$^{3'}$, —O—C(O)R$^{3'}$, —N(R$^{3'}$)$_2$—C(O)N(R$^{3'}$)$_2$, —N(R$^{3'}$)C(O)(R$^{3'}$)$_2$, —N(R$^{3'}$)C(O)N(R$^{3'}$)$_2$, —N(R$^{3'}$)C(O)OR$^{3'}$, —O—C(O)N(R$^{3'}$)$_2$, —N(R$^{3'}$)SO$_2$R$^{3'}$, —SO$_2$N(R$^{3'}$)$_2$ and —SO$_2$R$^{3'}$;

R$^{3'}$ is H or —C$_{1-6}$alkyl;

D is O, NCN or NSO$_2$C$_{1-3}$alkyl;

A is C, N or CH;

m and n are independently 0, 1 or 2;

provided that
  if m and n are 0, then A is not N;
  if m is 2, then n is not 2; or
    if n is 2, then m is not 2;

E is N, CH or C;

p is 0 or 1;
  if p is 1, then G, J and E together form A$^x$ or A$^y$;
    A$^x$ is a fused heterocycle having two fused rings with 5 to 7 members in each of said rings, said heterocycle containing one to four of the same or different heteroatoms selected from the group consisting of O, N and S; and
      optionally containing 1 or 2 carbonyls wherein the carbon atom of said carbonyl is a member of said fused heterocycle;
    A$^y$ is a 4 to 6 membered heterocycle containing one to three heteroatoms selected from the group consisting of O, N and S; and
      optionally containing 1 to 2 carbonyls, wherein the carbon atom of said carbonyl is a member of said 4 to 6 membered heterocycle;
    wherein A$^x$ and A$^y$ are optionally substituted with C$_{1-4}$alkyl, C$_{1-4}$alkoxy, C$_{1-4}$haloalkyl, cyano, C$_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino; or
  if p is 0 such that G and J are each attached to A, then A is C, and G, J and A together form a spirocyclic ring system with said rings of said system containing A and wherein GJA is A$^x$ or A$^y$ wherein said process comprises
  (a) coupling a compound of Formula IX

IX wherein
  R$^4$ is C$_{1-6}$alkyl or benzyl; and
  PG is BOC, CBZ, or FMOC
  with R$^3$X
    wherein
      R3 is as defined above; and
      X is bromo, iodo or a sulfonate selected from the group consisting of mesylate, tosylate and triflate to form a compound of Formula XI;

XI (b) hydrolyze said compound of Formula XI to form a compound of Formula XIII

XIII (c) reduce said compound of Formula XIII to form a compound of Formula XIV

XIV (d) react a compound of Formula XIV with a compound of Formula V

V in a mixed urea or urea isostere reaction to form a compound of Formula VII

VII (e) hydrolyzing said compound of Formula VII to form a compound of Formula VIII or a salt thereof; and

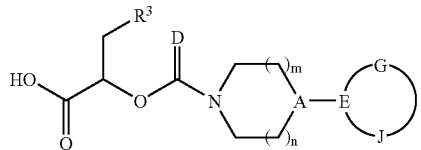

VIII (f) transforming the carboxylic acid moiety of said compound of Formula VIII to (V')$_t$V to form a compound of Formula Ib or a salt thereof.

According to a first embodiment of a fifth aspect of the invention is a process for synthesizing a compound of Formula II or VI

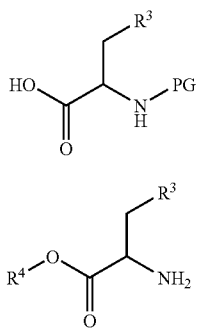

II

VI wherein

R$^3$ is indazolyl optionally substituted with 1 to 3 substituents selected from the group consisting of halo and C$_{1-6}$alkyl;

R$^4$ is C$_{1-6}$alkyl or benzyl; and

PG is BOC, CBZ or FMOC comprising (a) coupling a compound of Formula IX

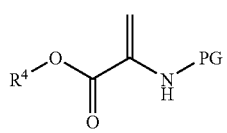

IX wherein

R$^4$ is C$_{1-6}$alkyl or benzyl; and

PG is BOC, CBZ, or FMOC with R$^3$X wherein

R$^3$ is phenyl optionally substituted with 1 to 3 substituents selected from the group consisting of amino, nitro, halo, and C$_{1-6}$alkyl; and X is bromo, iodo or a sulfonate selected from the group consisting of mesylate, tosylate and triflate to form a compound of Formula XI;

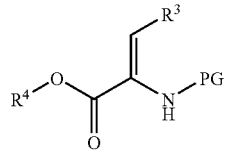

XI (b) reducing said compound of Formula XI to form a compound of Formula XII;

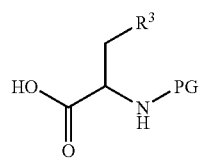

XII (c) transforming R$^3$ from said substituted phenyl to said substituted indazolyl; and deprotecting a compound of Formula XII to form a compound of Formula II or a compound of Formula VI or a salt thereof.

According to a second embodiment of the fifth aspect of the invention is a process for synthesizing a compound of Formula II or VI

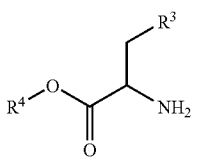

II

VI wherein

R$^3$ is 7-methyl-1H-indazol-5-yl;

R$^4$ is C$_{1-6}$alkyl or benzyl; and

PG is BOC, CBZ or FMOC comprising (a) coupling a compound of Formula IX

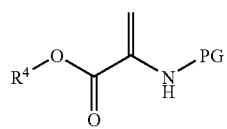

IX wherein
R⁴ is $C_{1-6}$alkyl or benzyl; and
PG is BOC, CBZ, or FMOC
with R³X
wherein
R³X is 4-iodo-2,6-dimethylaniline
to form a compound of Formula XI;

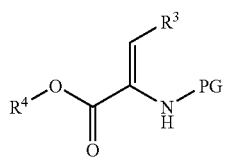

XI (b) reducing said compound of Formula XI to form a compound of Formula XII;

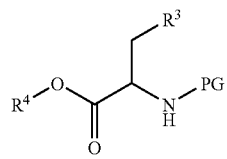

XII (c) transforming R³ from 2,6-dimethylanilin-3-yl to 7-methyl-1H-indazol-5-yl; and deprotecting a compound of Formula XII to form a compound of Formula II or a compound of Formula VI or a salt thereof.

According to a first embodiment of a sixth aspect of the invention is a process for synthesizing a compound of Formula XIV, XV, or XVI

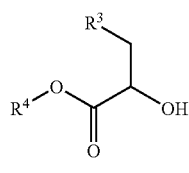

XIV

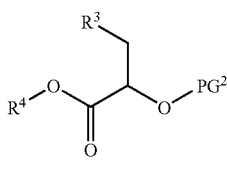

XV

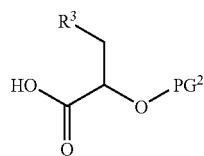

XVI wherein
R³ is indazolyl optionally substituted with 1 to 3 substituents selected from the group consisting of halo and $C_{1-6}$alkyl;
R⁴ is $C_{1-6}$alkyl or benzyl; and
PG² is methoxymethyl ether, benzyloxymethyl ether, benzyl or tri-$C_{1-6}$alkylsilyl;

comprising
(a) hydrolyzing a compound of Formula XI

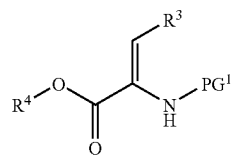

XI wherein
R⁴ is $C_{1-6}$alkyl or benzyl; and
PG¹ is BOC, CBZ or FMOC
to a compound of Formula XIII

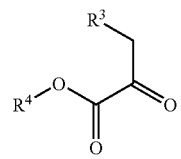

XIII (b) reducing said compound of Formula XIII to a compound of Formula XIV;

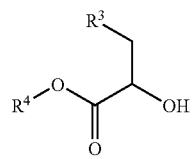

XIV (c) protecting the hydroxy moiety of compound XIV with PG²
wherein PG² is methoxymethyl ether, benzyloxymethyl ether, benzyl or tri-$C_{1-6}$alkylsilyl;
to form a compound of Formula XV; and

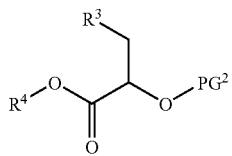

XV (d) hydrolyzing R⁴ to form a compound of Formula XVI.

According to a second embodiment of a sixth aspect of the invention is a process for synthesizing a compound of Formula XIV, XV, or XVI

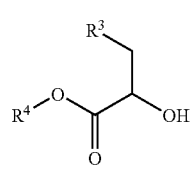

XIV

-continued

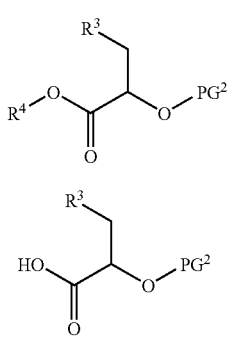

wherein
R³ is 7-methyl-1H-indazol-5-yl;
R⁴ is C₁₋₆alkyl or benzyl; and
PG² is methoxymethyl ether, benzyloxymethyl ether, benzyl or tri-C₁₋₆alkylsilyl;

comprising
(a) hydrolyzing a compound of Formula XI

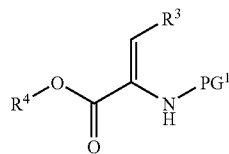

wherein R⁴ is C₁₋₆alkyl or benzyl;
PG¹ is BOC, CBZ or FMOC; and
R³ is 2,6-dimethylanilin-3-yl to form a compound of Formula XIII;

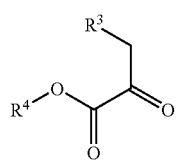

(b) reducing said compound of Formula XIII to a compound of Formula XIV;

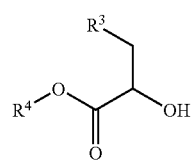

(c) protecting the hydroxy moiety of compound XIV with PG²
wherein PG² is methoxymethyl ether, benzyloxymethyl ether, benzyl or tri-C₁₋₆alkylsilyl;

to form a compound of Formula XV; and

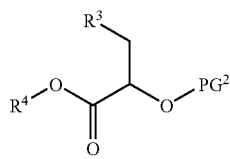

(d) hydrolyzing R⁴ to form a compound of Formula XVI.

DETAILED DESCRIPTION

The description of the invention herein should be construed in congruity with the laws and principles of chemical bonding. For example, it may be necessary to remove a hydrogen atom in order accommodate a substitutent at any given location.

As used herein, "heterocyclic," "heterocycle," "heterocyclo," and related terms include cyclic moieties containing one or more heteroatoms, (e.g., O, N or S) said heterocycles include those that are aromatic and those that are not, i.e., "alicyclic", unless otherwise specified.

As used herein, "aryl" includes both carbocyclic and heterocyclic aromatic ring systems and includes both monocyclic, bicyclic, and polycyclic ring systems.

As used herein, "heteroaryl" includes aromatic ring systems containing one or more heteroatoms, (e.g., O, N or S), that is heterocyclic ring systems. As used herein, the term "fused bicyclic system" when describing for example a 5,6-fused bicyclic system containing 1 to 4 nitrogen atoms includes aromatic and alicyclic systems, e.g. indolizine, indole, isoindole, 3H-indole, indoline, indazole or benzimidazole.

If a substitutent is named generically, then any and all species of that genus comprise that aspect of the invention. For example, a substituent generically named as "pyrrolonyl" (the radical of "pyrrolone", a pyrrole having a carbonyl) includes pyrrol-2-onyls wherein the carbonyl is adjacent to the nitrogen and pyrrol-3-onyls wherein the carbonyl and nitrogen have an intervening methylene.

Similarly, the present invention comprises that a substituent may be attached at any of all suitable points of attachment on said substituent unless otherwise specified. However, it is also understood that the compounds encompassed by the present invention are those that are chemically stable, i.e., heteroalicyclic substituents of the present invention should not be attached in such a way that a heteroatom in said heteroalicyclic substituent is alpha to a point of attachment wherein said point of attachment is also a heteroatom.

An embodiment or aspect which depends from another embodiment or aspect, will describe only the variables having values or provisos that differ from the embodiment or aspect from which it depends. If for example a dependent embodiment only addresses R2, then the variables and provisos not related to R2 should reflect that of the embodiment from which it depends.

If a variable is quantified with a value of zero, then a bond attaching said variable should no longer be represented.

As used herein, "alkylene" means a divalent alkane, i.e., an alkane having two hydrogen atoms removed from said alkane (said hydrogen removed from two different carbon atoms when said alkane contains more than one carbon atom), e.g., —CH2CH2CH2—.

As used herein, "alkylidene" means an alkane having two hydrogen atoms removed from one carbon atom in said alkane, e.g.,

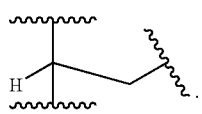

It should be understood that the alternating double bond designations in the six-membered ring of the 5,6-membered fused structure represented in Formula (I) are relative and represent the delocalized π orbital electrons of said ring.

As used herein, "halo" or "halogen" includes fluoro, chloro, bromo and iodo and further means one or more of the same or different halogens may be substituted on a respective moiety.

Unless specificied otherwise, acyclic hydrocarbons such as alkyl, alkoxy, alkenyl and alkynyl may be branched or straight chained.

Terms for protecting groups are as understood by practitioners in the field. "BOC" means t-butoxycarbonyl. "CBZ" means carbobenzyloxy. "FMOC" means 9-fluorenylmethoxycarbonyl.

It is to be understood that the present invention may include any and all possible stereoisomers, geometric isomers, diastereoisomers, enantiomers, anomers and optical isomers, unless a particular description specifies otherwise.

As used herein, "PG" means a protecting group. Appropriate protecting groups for functional groups are known in the art. See Greene, T. W. and Wutz, P. G. *Protective Groups in Organic Synthesis*; John Wiley & Sons: New York, 1999.

The compounds of this invention may exist in the form of salts. Such salts may include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group may exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. The compounds of the present invention may be solvated including hydrated and non-hydrated forms.

Synthesis

Compounds of the present invention may be synthesized according to the general schemas provided below. Variables provided in the schema below are defined in accordance with the description of compounds of the above Formula unless otherwise specified. Variations of said schemes may be used to prepare the compounds of the present inventions, said variations known to those of ordinary skill in the art.

Scheme 1. Synthesis of Formula I Compounds

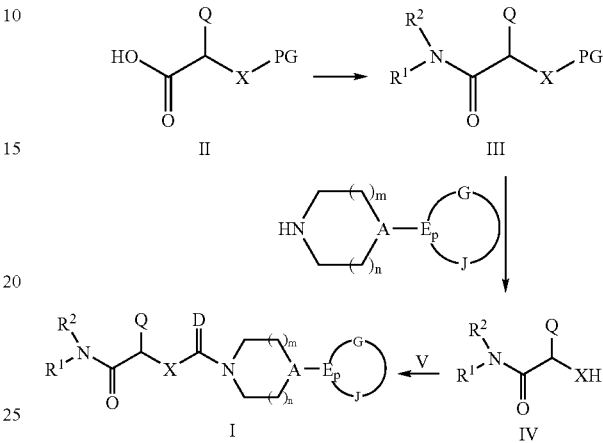

The synthesis described in Scheme 1 begins with a compound of Formula II, which is an amino acid (X=NH) or hydroxyl acid (X=O) with a protected amino or hydroxy terminus. Common amino protecting groups (PG) include BOC, CBZ, and FMOC and their addition and removal are known in the field. Common hydroxyl protecting groups (PG) include methoxymethyl ether, benzyloxymethylether, substituted benzyl groups and trialkylsilyl group and their addition and removal are known in the field. The carboxylic acid moiety of a Formula II compound can be coupled with an amine of formula $HNR^1R^2$ using standard peptide coupling reagents to form an amide of Formula III. The amino or hydroxy protecting group can be removed resulting in a Formula IV compound. This compound can then be coupled with an amine of Formula V in a mixed urea or urea isostere reaction, to generate a Formula I compound. Mixed urea formation can be conveniently carried using phosgene, disuccinimidyl carbonate, carbonyl diimidazole or other equivalents. Formation of urea isosteres, such as cyanoguanidines and sulfonylguanidines, are known in the art.

Scheme 2. Synthesis of Formula I Compounds

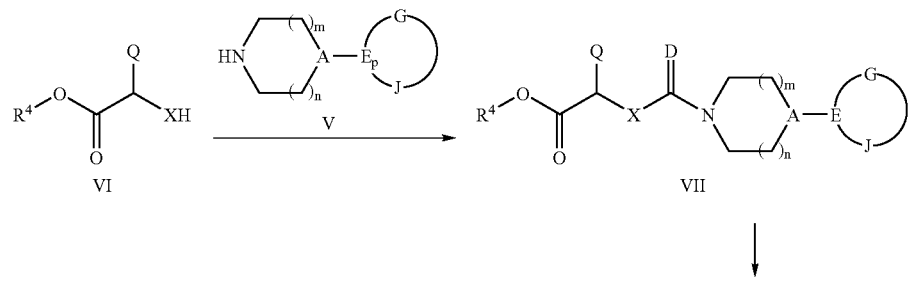

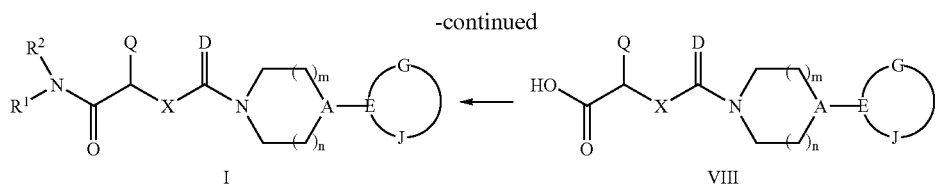

The synthesis described by Scheme 2 begins with a compound of Formula VI, which is an amino (X=NH) or hydroxy (X=O) ester. Methyl esters are commonly used but other esters which serve as protecting groups such as ethyl, t-butyl, and benzyl esters may also be employed. The Formula VI compound can be coupled with an amine of Formula V in a mixed urea or urea isostere reaction, as above, to generate a Formula VII compound. The Formula VII compound can be converted to a free acid compound of Formula VIII which can then be coupled with an amine of Formula $HNR^1R^2$ to generate a Formula I compound.

Scheme 3. Synthesis of Formula II and VI Compounds

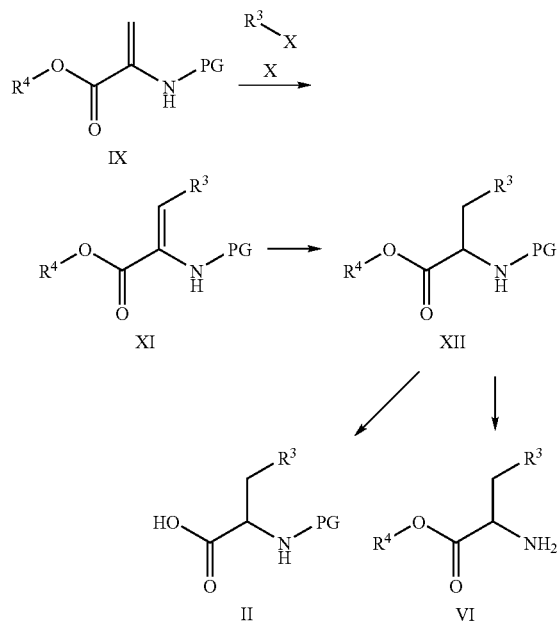

N-Protected amino acids of Formula II and amino esters of Formula VI can be prepared according to Scheme 3. An N-protected aminoacrylate of Formula IX can be coupled to a compound of Formula X where $R^3$ is an aromatic ring and X is a leaving group. Some leaving groups include halogens such as iodine, bromine, and chorine and sulfonates such as mesylate, tosylate, and triflate. The coupling typically occurs in the presence of a transition metal complex and a base and may contain additives. A variety of transition metal catalyst and precatalyst complexes can be used. Some examples of the transition metal are palladium (0) and palladium (II). Some examples of ligands used in the complex are carboxylates (such as acetate and trifluoroacetate), halogens (such as chloro), dibenzylideneacetone, acetonitrile, allyl, and phosphines such as triphenylphosphine and tritolylphosphine. Some other phosphine ligands include TFP, $PCy_3$, di-t-butylphosphanylbiphenyl, dppe, dppp, dppb, dppf, and BINAP.

Some bases include carboxylates (such as acetate), alkoxides (such as t-butoxide and pivalyloxide), bicarbonate, carbonate, phophate, and amine bases such as triethylamine, Hunig's base, PMP, proton sponge, TMEDA, and DBU. Some additives include salts of silver, thallium, halides, and alcohols. Some suitable solvents include THF, DMF, NMP, DMA, acetonitrile, toluene, benzene, DCE, ethanol, methanol, and water. The reaction can vary between room temperature and reflux depending on the catalyst system used. See Link, J. T, *Org. React.* 2002, 60, 157-534 and references cited therein for some appropriate conditions.

The double bond of the resulting Formula XI compound can be reduced to give compounds of Formula XII. Reduction can be carried out to give either a racemate or by use of a stereoselective catalyst to give either optical enantiomer of Formula XII. Such reductions can result from transfer hydrogenation from hydrogen donors such as formic acid or cyclohexadiene, or hydrogenation using gaseous hydrogen, both in the presence of a suitable catalyst. See Berens, U. et al. *Angew. Chem. Int. Ed.* 2000, 39, 1981 and Burk, M. J. *Acc. Chem. Res.* 2000, 33, 363 and references cited therein for some stereoselective catalyst systems. Compounds of Formula XII can be further transformed to either free amines of Formula VI by removal of the amino protecting group (PG) under appropriate conditions, or to free acids of Formula II by selective hydrolysis of the methyl ester using, for example, lithium hydroxide in a protic solvent at room temperature. Although methyl esters are shown in Scheme 3, other esters such as ethyl, tert-butyl and benzyl could be similarly employed. The $R^3$ aromatic ring of Formula XII compounds may be further transformed to give other amino acid derivatives of Formula XII using organic chemical manipulations known in the art.

Compounds of Formula XI can also be used to prepare hydroxyesters of Formula XIV as shown in Scheme 4.

Scheme 4. Synthesis of Formula XIV and XVI Compounds

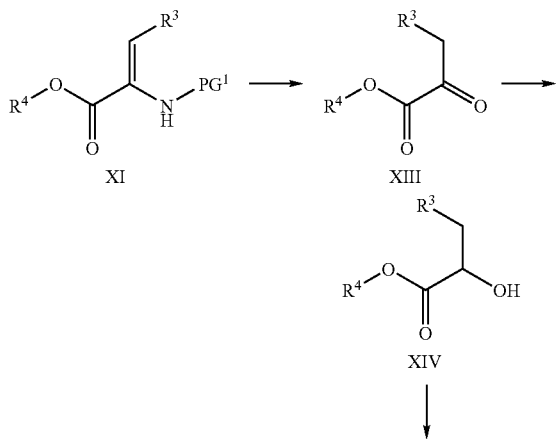

-continued

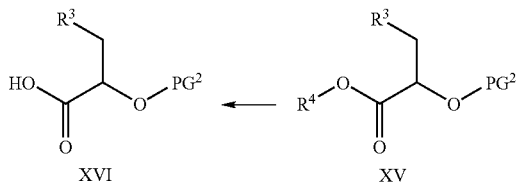

XVI  XV

The compound of Formula XI can be converted to a alpha-ketoester of Formula XIII by removal of the amino protecting group (PG$^1$) followed by hydrolysis. The alpha-ketoester of Formula XIII can be reduced to give a compound of Formula XIV by an appropriate reducing agent, such reducing agents are known in the art. The hydroxyl of a compound of Formula XIV can be protected to give an appropriate hydroxyl protected terminus of Formula XV. Common hydroxyl protecting groups (PG$^2$) include methoxymethyl ether, benzyloxymethylether, substituted benzyl groups and trialkylsilyl group and their addition and removal are known in the field. A compound of Formula XV can be converted to a compound of Formula XVI by treatment with lithium hydroxide, sodium hydroxide, or other organic or inorganic bases using water or other suitable solvents using methodology known in the art.

Compounds of Formula VII can also be used to prepare oxadiazole-containing compounds of Formula I may be prepared according to Scheme 5.

Scheme 5. Synthesis of Formula I Compounds

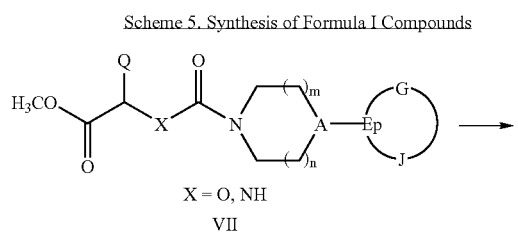

X = O, NH
VII

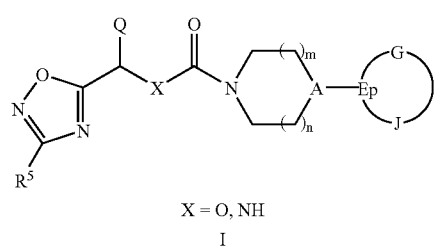

X = O, NH
I

Treatment of N-hydroxyamidines with bases such as sodium hydride followed by addition of esters of Formula VII and heating can generatae [1,2,4]oxadiazoles of Formula I, generally after heating.

Compounds of Formula VII can also be used to prepare tetrazole-containing compounds of Formula I may be prepared according to Scheme 6.

Scheme 6. Synthesis of Formula I Comounds

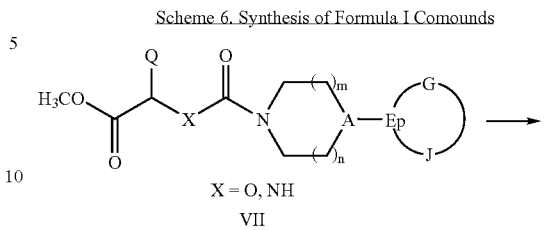

X = O, NH
VII

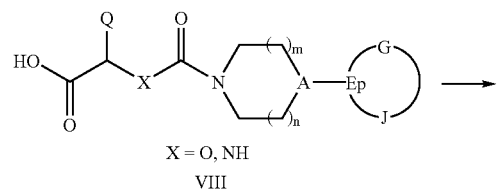

X = O, NH
VIII

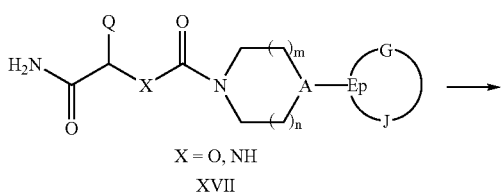

X = O, NH
XVII

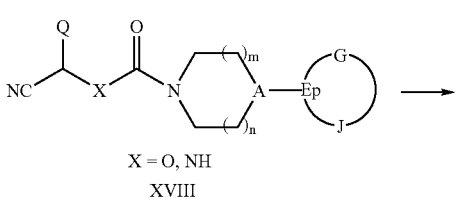

X = O, NH
XVIII

X = O, NH
I

Esters of Formula VII can be hydrolyzed to the corresponding carboxylic acids using either acids or bases, controlling conditions to spare other functionality. Acids of Formula VIII can be converted to the primary amides of Formula XVII by simple coupling with ammonia using various amide coupling agents well known in the art. Nitriles of Formula XVIII are available from the amides by dehydration using agents such as trifluoroacetic anhydride. These can be converted to the corresponding tetrazoles of Formula I (where R$^5$=H) by treatment with azidotrimethyltin. Deprotonation of these compounds with bases such as sodium hydride, followed by alkylation with various agents such as alkyl halides and alkyl sulfonates gives further compounds of Formula I that are substituted on the tetrazole ring.

Imidazole-containing compounds of Formula I can be prepared according to Scheme 7.

Scheme 7. Synthesis of Formula I Compounds

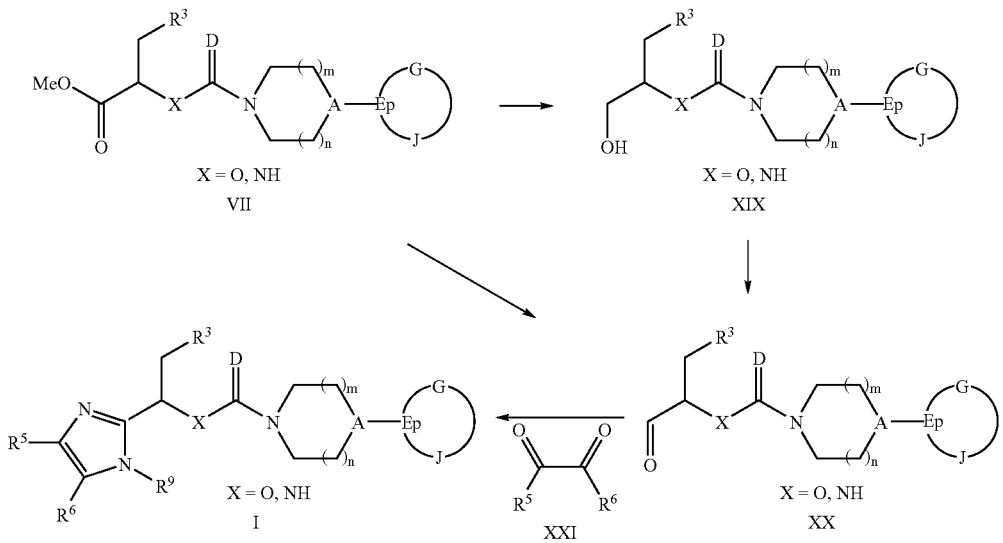

The synthesis described by Scheme 7 begins with an ester of Formula VII. The ester may be reduced directly to an aldehyde of Formula XX using diisobutylaluminum hydride or other appropriate reducing agent. Alternately, compounds of Formula VII can be reduced to an alcohol of Formula XIX by using lithium borohydride or another appropriate reducing agent. Alcohols of Formula XIX can be oxidized to aldehydes of Formula XX by treatment with an appropriate oxidant. Such oxidations and reductions are well known to those skilled in the art. Aldehydes of Formula XX can be condensed with dicarbonyl compounds of Formula XXI in the presence of ammonia to afford N-unsubstituted imidazoles ($R^7$=H) of Formula I. These Formula I compounds can be further derivatized by alkylation with appropriate electrophiles such as alkyl halides or alkyl sulfonates in the presence of a base or aryl halides in the presence of a base and an appropriate catalyst to give Formula I compounds where $R^7$ is not H. In cases where a protecting group is employed on the group $R^3$, deprotection conditions appropriate to the protecting group and compatible with the rest of the molecule can be employed to remove it. Such protecting group manipulations are well known to those skilled in the art.

Imidazole-containing compounds of Formula I can also be prepared according to Scheme 8.

Scheme 8. Synthesis of Formula I Compounds

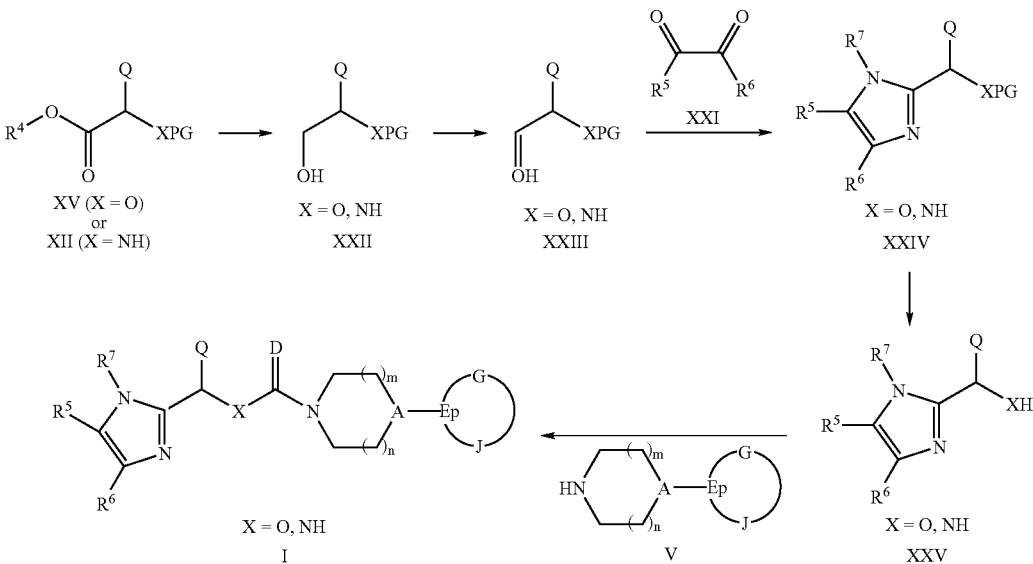

Scheme 8 begins with reduction of an alkyl ester of Formula XV or Formula XII to an alcohol of Formula XXII using an appropriate reducing reagent such as lithium borohydride. The resulting alcohol can then be oxidized to an aldehyde of Formula XXIII by treatment with an appropriate oxidant. In some cases it is possible to reduce compounds of Formula XV or Formula XII directly to compounds of Formula XXIII by use of diisobutylaluminum hydride or another appropriate reducing agent. Such oxidations and reductions are well known to those skilled in the art. The Formula XXIII aldehyde can be condensed with a Formula XXI dicarbonyl compound to afford an N-unsubstituted ($R^7$=H) imidazole of Formula XXIV. In some cases, it is desirable to alkylate the imidazole with an appropriate electrophilic reagent such as alkyl halides or alkyl sulfonates in the presence of a base, or aryl halides in the presence of a base and an appropriate catalyst to afford substituted imidazoles of Formula XXIV where $R^7$ is not H. The protecting group (PG) can then be removed to liberate the hydroxyl group (when X=O) or the primary amine (when X=NH) by application of deprotection conditions appropriate to the protecting group. Such deblocking conditions are well known in the art. Compounds of Formula XXV can be coupled with an amine of Formula V in the presence of phosgene or a phosgene equivalent to generate a urethane (when X=O) or mixed urea (when X=NH) of Formula I. Compounds of Formula XXV can also be used in a urea isostere reaction, as above, to generate a Formula I compound. Where protecting groups have been utilized on the group Q, they are removed by conditions appropriate to the protecting group and compatible with the rest of the molecule.

Tetrazole-containing compounds of Formula I may also be prepared according to Scheme 9.

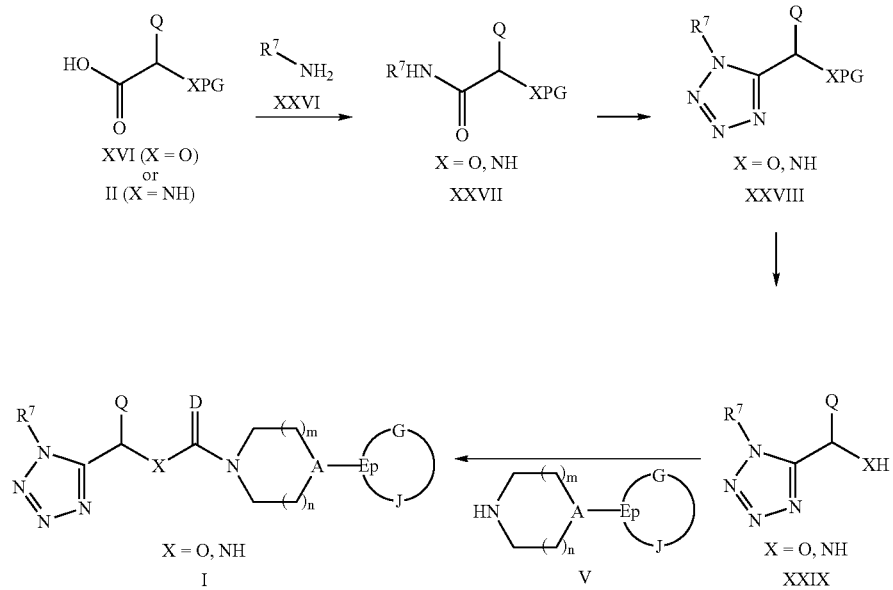

Scheme 9. Synthesis of Formula I Compounds

Scheme 9 begins with the coupling of a carboxylic acid of Formula XVI or Formula II to a primary amine of Formula XXVI to give secondary amides of Formula XXVII using various amide coupling agents well known in the art. Conversion of Formula XXVII amides to tetrazoles of Formula XXVIII can be accomplished by treatment with a dehydrating agent such as phosphorous pentachloride or phosphorous oxychloride followed by treatment with an azide source such as tributyltin azide. The protecting group (PG) can then be removed to liberate the hydroxyl group (when X=O) or the primary amine (when X=NH) by application of deprotection conditions appropriate to the protecting group. Such deprotections are well known in the art. Resulting compounds of Formula XXIX can be coupled with an amine of Formula V in the presence of phosgene or a phosgene equivalent to generate a urethane (when X=O) or mixed urea (when X=NH) of Formula I. Compounds of Formula XXIX can also be used in a urea isostere reaction, as above, to generate Formula I compounds. Where protecting groups have been utilized on Q, they are removed by conditions which are appropriate to the protecting group.

Compounds of Formula I may also be prepared according to Scheme 10.

Scheme 10. Synthesis of Formula I Compounds

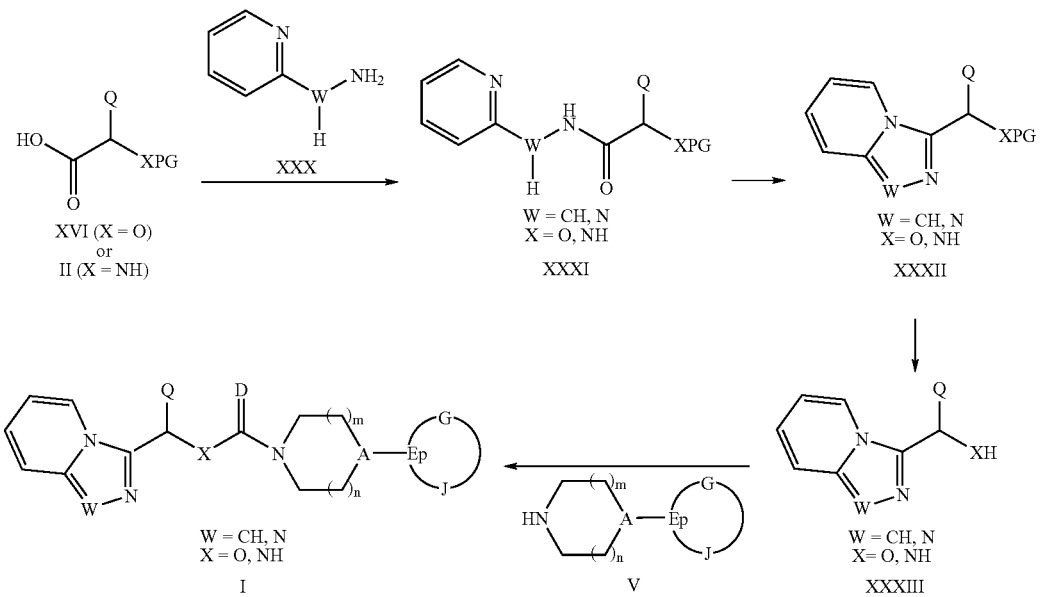

Scheme 10 begins with the coupling of a carboxylic acid of Formula XVI or Formula II to a compound of Formula XXX to give secondary amides of Formula XXXI using various amide coupling agents well known in the art. The pyridinyl-amide of Formula XXXI can be made to undergo cyclization to give heterocycles of Formula XXXII by use of a dehydrating agent such as phosphorous pentachloride or phosphorous oxychloride either alone or in the presence of an amine base such as pyridine or quinoline. The protecting group (PG) can then be removed to liberate the hydroxyl group (when X=O) or the primary amine (when X=NH) by application of deprotection conditions appropriate to the protecting group. Such deprotections are well known in the art.

Compounds of Formula XXXIII are coupled with an amine of Formula V in the presence of phosgene or a phosgene equivalent to generate a urethane (when X=O) or mixed urea (when X=NH) of Formula I. Compounds of Formula XXXIII can also be used in a urea isostere reaction, as above, to generate Formula I compounds. Where protecting groups have been utilized on Q, they can be removed by conditions which are appropriate to the protecting group and compatible with the rest of the molecule.

$^1$H— and $^{13}$C-NMR spectra were run on a Bruker 500 or 300 MHz instrument and chemical shifts were reported in ppm (δ) with reference to tetramethylsilane (δ=0.0). All evaporations were carried out under reduced pressure. Unless otherwise stated, LC/MS analyses were carried out on a Shimadzu instrument using a YMC C18 column (3×50 mm) employing a 2 min linear gradient of 0% to 100% solvent B in A in a 3 min run. For LC/MS and for Shimadzu Preparative HPLC system, Solvent A-was: 10% methanol/90% water/ 0.1% trifluoroacetic acid, and solvent B was 90% methanol/ 10% water/0.1% trifluoroacetic acid with a UV detector set at 220 nm.

4-Iodo-2,6-dimethylbenzenamine hydrochloride

To a suspension of sodium bicarbonate (126 g, 1500 mmol) and 2,6-dimethylaniline (61.5 mL, 500 mmol) in methanol (700 mL) was added iodine monochloride (1.0 M in dichloromethane, 550 mL, 550 mmol) at room temperature over 1 h. After addition was complete, stirring was continued for 3 h. The reaction was filtered to remove excess sodium bicarbonate and the solvent removed in vacuo. The residue was redissolved in diethyl ether (1.5 L) and treated with hydrochloric acid (2M in ether, 375 mL, 750 mmol). The resulting suspension was stored in the freezer (−15° C.) overnight. The solid was filtered and washed with diethyl ether until it became colorless to give 126.5 g (89%) as a grey-green powder. $^1$H-NMR (DMSO-d$_6$) δ 2.33 (s, 6H), 7.48 (s, 2H), 9.05 (bs, 3H); $^{13}$C-NMR (DMSO-d$_6$) δ 17.4, 91.5, 133.1, 131.2, 136.9.

Methyl 2-(benzyloxycarbonyl)acrylate

To a flame dried three-neck round bottom flask, fitted with a mechanical stirrer, was added (S)-methyl 2-(benzyloxycarbonyl)-3-hydroxypropanoate (129 g, 509 mmol), anhydrous dichloromethane (2 L), and methanesulfonyl chloride (49.3 mL, 636 mmol). The mixture was cooled to −15° C., and treated with triethylamine (213 mL, 1527 mmol), dropwise, to ensure the temperature of the reaction mixture did not exceed 0° C. (The addition of the first equivalent of triethylamine was exothermic.) After addition of triethylamine, the mixture was stirred at 0° C. for 30 min. The cooling bath was removed and the mixture stirred at room temperature for 1.5 h. The reaction was quenched by addition of methanol (21 mL). The mixture was washed with 0.5% aqueous potassium bisulfate until the washings were pH 5, then saturated sodium bicarbonate, and brine, dried over sodium sulfate, and concentrated. Flash chromatography (silica gel, 1:9 ethyl acetate/hexanes) gave 111 g (92%) as a viscous colorless oil, which crystallized upon standing. $^1$H-NMR (DMSO-$d_6$) δ 3.71 (s, 3H), 5.10 (s, 2H), 5.60 (s, 1H), 5.76 (s, 1H), 7.39-7.35 (m, 5H), 8.96 (s, 1H); $^{13}$C-NMR (DMSO-$d_6$) δ 52.3, 65.9, 127.8, 128.1, 128.3, 128.8, 133.3, 136.3, 153.5, 163.7.

(Z)-Methyl 3-(4-amino-3,5-dimethylphenyl)-2-(benzyloxycarbonyl)acrylate

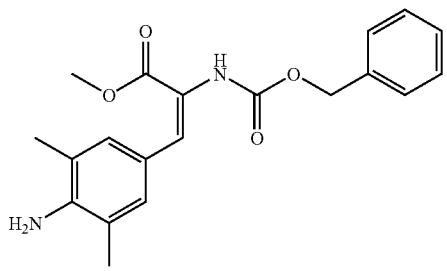

A 2 L round bottom flask was charged 4-iodo-2,6-dimethylbenzenamine hydrochloride salt (55 g, 194 mmol), methyl 2-(benzyloxycarbonyl)acrylate (59.2 g, 252 mmol), tetrabutylammonium chloride (59.2 g, 213 mmol), palladium (II) acetate (4.34 g, 19.4 mmol), and tetrahydrofuran (1.2 L, degassed by a flow of nitrogen for 30 min). The mixture was stirred so that a suspension was formed and then degassed by a flow of nitrogen for 30 min. Triethylamine (10 mL, 789 mmol) was added and the resulting mixture was heated at reflux for 3 h. After cooling to room temperature, the reaction mixture was filtered through a pad of celite, washed with tetrahydrofuran (2×100 mL), and concentrated. The residue was dissolved in dichloromethane, washed with water (3×) and brine (2×), dried over sodium sulfate, and concentrated. Flash chromatography (silica gel using 1:9 ethyl acetate/dichloromethane) gave a tan solid. The solid was recrystallized from warm methanol (210 mL) and water (100 mL). The mixture was held at room temperature overnight, then at 0° C. for 2 h, and finally at −15° C. for 2 h. The resulting solid was filtered, washed with ice cold 1:1 methanol/water, and dried under high vacuum overnight to give 44.7 g (65%) as a light tan solid which was a mixture of Z/E isomers (73:27). $^1$H-NMR (DMSO-$d_6$) δ, 2.05 (s, 6H), 3.61 (s, 0.8H), 3.68 (s, 2.2H), 5.00 (s, 0.54H), 5.13 (s, 1.46H), 5.24 (s, 2H), 7.40-7.21 (m, 8H), 8.51 (s, 0.27H), 8.79 (s, 0.73H); $^{13}$C-NMR (DMSO-$d_6$) δ 17.8, 51.7, 65.3, 119.4, 120.0, 120.3, 127.3, 127.7, 128.3, 130.9, 135.8, 137.2, 146.9, 154.7, 166.0.

(R)-Methyl 3-(4-amino-3,5-dimethylphenyl)-2-(benzyloxycarbonyl)propanoate

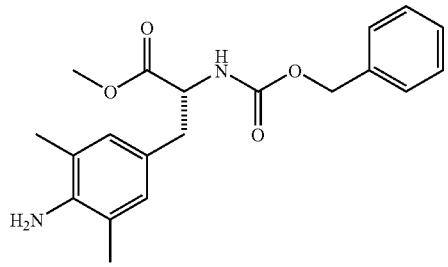

A flame-dried 2 L Parr hydrogenation bottle was charged with (Z)-methyl 3-(4-amino-3,5-dimethylphenyl)-2-(benzyloxycarbonyl)acrylate (84.5 g, 239 mmol), dichloromethane (300 mL), and methanol (300 mL). The bottle was swirled so that a light brown suspension was formed. This was degassed by a flow of nitrogen for 30 min. To this was quickly added (−)-1,2-bis((2R,5R)-2,5-diethylphospholano)bezene(cyclooctadiene) rhodium (I) tetrafluoroborate ([(2R,5R)-Et-DuPhosRh]BF$_4$) (2.11 g, 3.20 mmol). The bottle was immediately attached to a Parr Hydrogenator. After 5 cycles of hydrogen (60 psi) and vacuum, the bottle was pressurized to 65 psi and the suspension was agitated at room temperature for 16 h. The reaction had become homogeneous. The reaction mixture was concentrated, and the resulting residue purified by flash chromatography (silica gel, 1:9 ethyl acetate/dichloromethane) to give 82.9 g (98%). $^1$H-NMR (DMSO-$d_6$) δ 2.04 (s, 6H), 2.65 (dd, J=13.4, 9.8 Hz, 1H), 2.82 (dd, J=13.7, 5.2 Hz, 1H), 3.62 (s, 3H), 4.15-4.10 (m, 1H), 4.41 (s, 2H), 5.00 (s, 2H), 6.68 (s, 2H), 7.37-7.28 (m, 5H), 7.70 (d, J=7.9 Hz, 1H); $^{13}$C-NMR (DMSO-$d_6$) δ 17.7, 35.9, 51.7, 56.1, 65.3, 120.4, 124.0, 127.5, 127.7, 128.2, 128.3, 136.9, 142.6, 155.9, 172.5.

(R)-Methyl 2-(benzyloxycarbonyl)-3-(7-methyl-1H-indazol-5-yl)propanoate

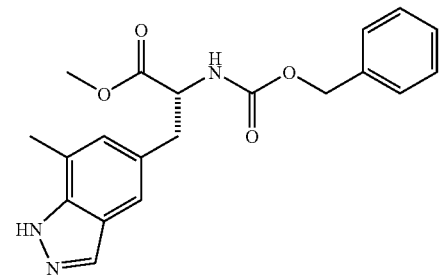

(R)-Methyl 3-(4-amino-3,5-dimethylphenyl)-2-(benzyloxycarbonyl)propanoate (50.0 g, 140 mmol) was weighed into a flame-dried 5 L three neck round bottom flask, followed by the addition of toluene (2400 mL) and glacial acetic acid (120 mL, 2096 mmol). The mixture was mechanically stirred to form a clear solution, and then potassium acetate (103 g, 1048 mmol) was added. To this white suspension, iso-amyl nitrite (20.7 mL, 154 mmol) was added dropwise at room temperature and the resulting mixture was stirred for 16 h. Saturated sodium bicarbonate (1 L) was added, followed by the careful addition of solid sodium bicarbonate to neutralize the acetic acid. The mixture was extracted with a mixture of dichloromethane (2 L) and brine (1.5 L). After separation, the aqueous layer was extracted with dichloromethane (500 mL). The combined organic layers were dried over anhydrous sodium sulfate and filtered. Solvents were removed to afford a tan solid, which was washed with hexanes (2.0 L) and toluene (150 mL). The solid was recrystallized from hot acetone (260 mL) and hexanes (700 mL). The slightly cloudy mixture was allowed to cool to room temperature slowly, then to 0° C. for 1.5 h, and finally to −15° C. for 1.5 h. The resulting solid was filtered and washed with ice-cold acetone/hexanes (1:1, 200 mL) to afford 39.1 g (76%). Analytical HPLC showed >98% UV purity. The enantiomeric excess was determined to be 99.8% (conditions: Chiralpak AD column, 4.6× 250 mm, 10 µm; A=ethanol, B=0.05% diethylamine/heptane; 85% B@1.0 mL/min. for 55 min. The retention times for R was 44.6 min and for S was 28.8 min). $^1$H-NMR (DMSO-d$_6$) δ 2.48 (s, 3H), 2.93 (dd, J=13.4, 10.7 Hz, 1H), 3.10 (dd, J=13.7, 4.9 Hz, 1H), 3.63 (s, 3H), 4.32-4.27 (m, 1H), 4.97 (s, 2H), 7.03 (s, 1H), 7.24-7.22 (m, 2H), 7.29-7.27 (m, 3H), 7.41 (s, 1H), 7.83 (d, J=8.2 Hz, 1H), 7.99 (s, 1H), 13.1 (s, 1H); $^{13}$C-NMR (DMSO-d$_6$) δ 16.7, 36.5, 51.8, 56.0, 65.3, 117.6, 119.6, 122.7, 127.2, 127.4, 127.6, 128.2, 129.3, 133.4, 136.8, 139.2, 155.9, 172.4. Mass spec.: 368.16 (MH)$^+$.

(R)-Methyl 2-amino-3-(7-methyl-1H-indazol-5-yl)propanoate

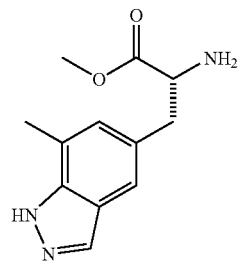

A Parr hydrogenation bottle was charged with (R)-methyl 2-(benzyloxycarbonyl)-3-(7-methyl-1H-indazol-5-yl)propanoate (11.0 g, 29.9 mmol) and methanol (75 mL). The suspension was purged with nitrogen and treated with palladium (10% on charcoal, 700 mg). The bottle was shaken under hydrogen (15 psi) overnight. The mixture was filtered through celite to remove catalyst. Concentration of the eluent gave 7.7 g (quant.) as an oil which was used without purification. $^1$H-NMR (CD$_3$OD) δ 2.54 (s, 3H), 2.98 (dd, J=13.5, 7.0 Hz, 1H), 3.09 (dd, J=13.5, 5.9 Hz, 1H), 3.68 (s, 3H), 3.75 (dd, J=7.0, 6.2 Hz, 1H), 7.01 (s, 1H), 7.39 (s, 1H), 7.98 (s, 1H). Mass spec.: 232.34 (M-H)$^−$.

(R)-Methyl-2-(4-(2-oxo-1,2-dihydroquinazolin-3(4H)-yl)piperidine-1-carboxamido)-3-(7-methyl-1H-indazol-5-yl)propanoate

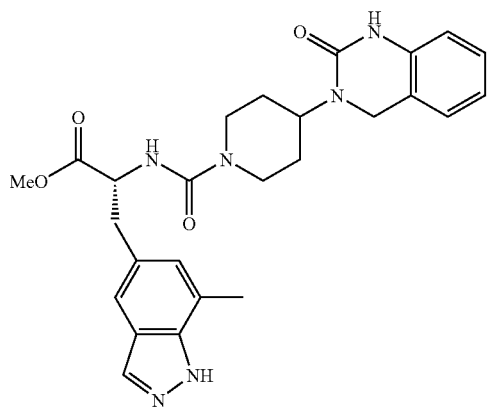

To a solution of (R)-methyl 2-amino-3-(7-methyl-1H-indazol-5-yl)propanoate (1.07 g, 4 mmol) and diisopropylethylamine (2.09 mL, 12 mmol) in dimethylformamide (15 mL) at room temperature was added N,N-disuccinimidyl carbonate (0.52 g, 4 mmol). The resulting mixture was stirred at room temperature for 30 min and treated with 3-(piperidin-4-yl)-3,4-dihydroquinazolin-2(1H)-one (0.92 g, 4 mmol) in portions. The reaction was stirred for 24 h. The mixture was concentrated, and the residue was purified by flash chromatography (silica gel, 30:1 dichloromethane/methanol 60:1, 30:1) to give 2 g (100%). Mass spec.: 491.38 (MH)$^+$, HPLC t$_R$=2.25.

(R)-2-(4-(2-oxo-1,2-dihydroquinazolin-3(4H)-yl)piperidine-1-carboxamido)-3-(7-methyl-1H-indazol-5-yl)propanoic acid

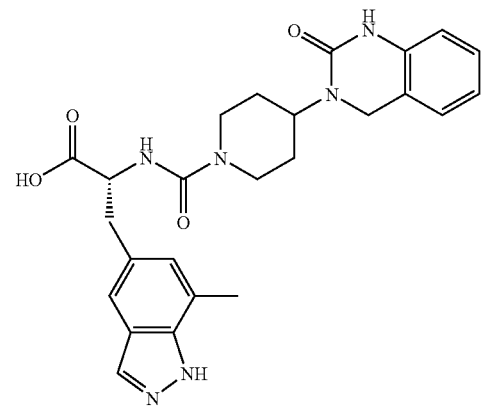

A stirred solution of (R)-methyl-2-(4-(2-oxo-1,2-dihydroquinazolin-3 (4H)-yl)piperidine-1-carboxamido)-3 (7-methyl-1H-indazol-5-yl)propanoate (2.24 g, 4.57 mmol) in 1:1 tetrahydrofuran/methanol (25 mL) was cooled to 0° C. To this mixture was added 2N lithium hydroxide (11.4 mL, 22.8 mmol) in several portions. The reaction mixture was stirred at room temperature for 4.5 h, and then more lithium hydroxide solution (2 mL) was added. Stirring was continued for a further 3 h, and then the mixture was stored at 0° C. overnight. The mixture was concentrated in vacuo and the resulting residue was dissolved in water, cooled to 0° C., and treated with cold 6N hydrochloric acid at 0° C. until pH 2 was attained. The resulting precipitate was collected by filtration, washed with cold water and ether, and then dried under high vacuum overnight to give 1.53 g (80%) as a white solid. Mass spec.: 477.31 (MH)⁺. HPLC $t_R$=1.87.

EXAMPLE 1

(R)-N-(1-(octahydroisoquinolin-2(1H)-yl)-3-(7-methyl-1H-indazol-5-yl)-1-oxopropan-2-yl)-(4-(2-oxo-1,2-dihydroquinnazolin-3(4H)-yl)piperidine-1-carboxamide

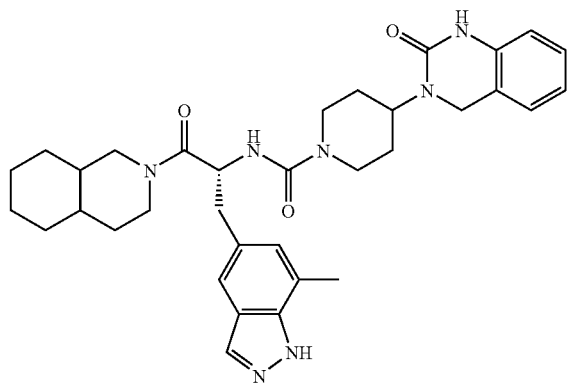

A flask was charged with (R)-2-(4-(2-oxo-1,2-dihydroquinazolin-3(4H)-yl)piperidine-1-carboxamido)-3-(7-methyl-1H-indazol-5-yl)propanoic acid (47.6 mg, 0.1 mmol), diisopropylethylamine (87 µL, 0.5 mmol), decahydroisoqunoline(45 mg, 0.3 mmol), and dimethylformamide (2 mL). The solution was cooled to 0° C., and treated with PyBOP® (57.2 mg, 0.11 mmol) in several portions. The reaction was allowed to gradually warm to room temperature overnight. The mixture was concentrated under reduced pressure. The residue was purified using preparative HPLC, to give 56 mg (79%) as the trifluoroacetate salt. Mass spec.: 598.54 (MH)⁺, HPLC $t_R$=2.71.

The following Examples were similarly prepared:

EXAMPLE 2

(R)-N-(1-(ethyl(pyridin-4-ylmethyl)amino)-3-(7-methyl-1H-indazol-5-yl)-1-oxopropan-2-yl)-(4-(2-oxo-1,2-dihydroquinnazolin-3(4H)-yl)piperidine-1-carboxamide

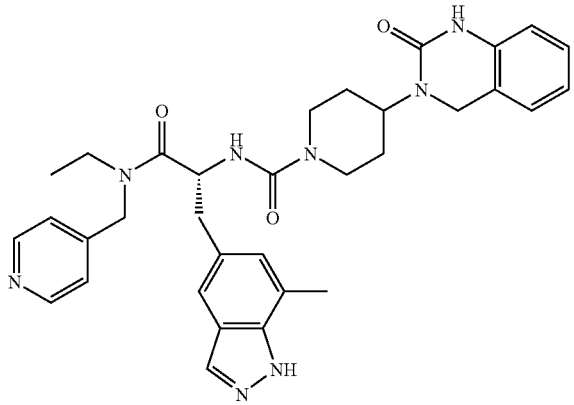

Yield: 64%. Mass spec.: 595.32 (MH)⁺, HPLC $t_R$=1.73.

EXAMPLE 3

(R)-N-(1-(4-cyclohexylpiperazin-1-yl)-3-(7-methyl-1H-indazol-5-yl)-1-oxopropan-2-yl)-(4-(2-oxo-1,2-dihydroquinnazolin-3(4H)-yl)piperidine-1-carboxamide

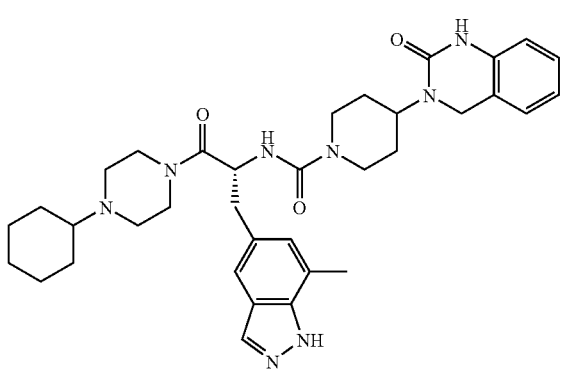

Yield: 63%) Mass spec.: 627.29 (MH)⁺, HPLC $t_R$=1.69.

EXAMPLE 4

(R)-N-(1-(benzylmethylamino)-3-(7-methyl-1H-indazol-5-yl)-1-oxopropan-2-yl)-(4-(2-oxo-1,2-dihydroquinnazolin-3(4H)-yl)piperidine-1-carboxamide

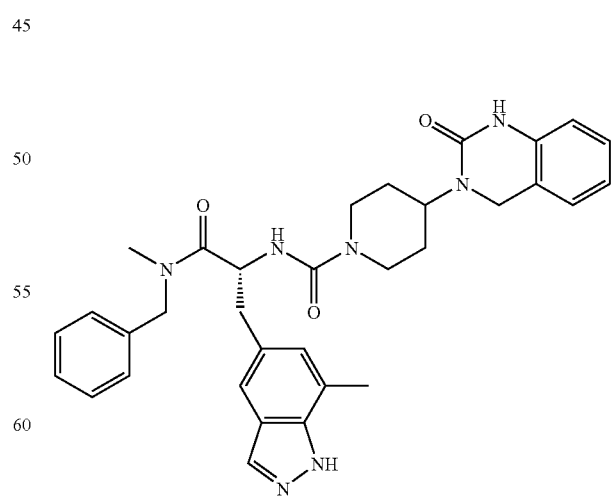

Yield: 67% Mass spec.: 580.23 (MH)⁺, HPLC $t_R$=2.22.

EXAMPLE 5

(R)-N-(1-(2-(dimethylamino)ethylamino)-3-(7-methyl-1H-indazol-5-yl)-1-oxopropan-2-yl)-(4-(2-oxo-1,2-dihydroquinnazolin-3(4H)-yl)piperidine-1-carboxamide

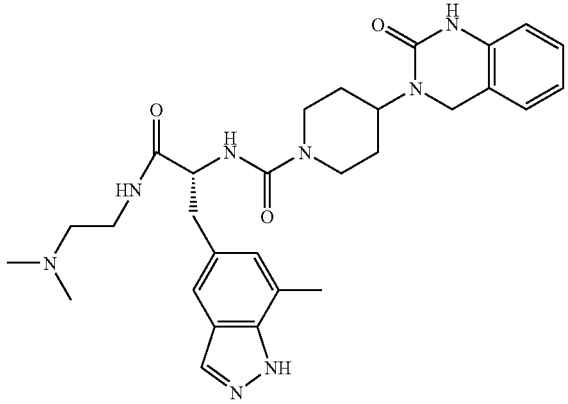

Yield: 57%. Mass spec.: 547.51(MH)+, HPLC $t_R$=1.30.

(R)-Benzyl 3-(7-methyl-1H-indazol-5-yl)-1-oxo-1-(pyridin-2-ylmethylamino)propan-2-ylcarbamate

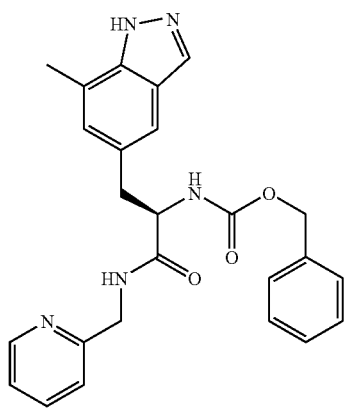

2-(Benzyloxycarbonyl)-3-(7-methyl-1H-indazol-5-yl)propanoic acid (0.47 g, 1.32 mmol), hydroxybenzotriazole (0.2 g, 1.46 mmol), 1-(3-dimethyl aminopropyl)-3-ethyl carbodiimide hydrochloride (0.28 g, 1.46 mmol), and 2-picolyl amine (0.56 mL, 1.46 mmol) were combined in ethyl acetate (10.0 mL). To this solution was added triethylamine (0.56 mL, 4.0 mmol) and the reaction mixture stirred at 40° C. for 2 h. After cooling to room temperature, the reaction mixture was diluted with ethyl acetate, washed with 5% citric acid (2×), brine (2×), dried over sodium sulfate, and concentrated to afford 0.42 g (72%).

Mass spec.: 444.4 (MH)+.

(R)-Benzyl 1-(H-imidazo[1,5-a]pyridin-3-yl)-2-(7-methyl-1H-indazol-5-yl)ethylcarbamate

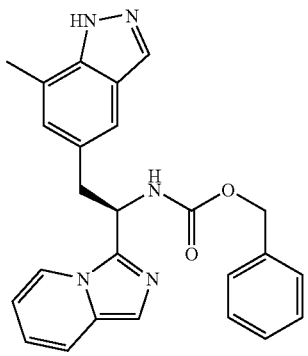

To a solution of benzyl 3-(7-methyl-1H-indazol-5-yl)-1-oxo-1-(pyridin-2-ylmethylamino)propan-2-ylcarbamate (75 mg, 0.17 mmol) in 1,2-dichloroethane (1.5 mL) was added phosphorus oxychloride (78 µL, 0.85 mmol) and pyridine (0.25 mL, 0.85 mmol). The reaction mixture was heated at reflux for 1 h, cooled to room temperature, and concentrated. The resulting residue was partitioned between ethyl acetate and saturated sodium bicarbonate. The organic layer was separated, washed with water (2×), brine (2×), dried over sodium sulfate, and concentrated to afford 22 mg (30%). $^1$H-NMR (CD$_3$OD, 300 MHz) δ 2.42 (s, 3H), 3.44 (s, 1H), 3.46 (s, 1H), 4.82-5.08 (m, 2H), 5.46 (m, 1H), 6.50 (m, 1H), 7.99 (d, J=6.2, 1H). Mass spec.: 426.20 (MH)+.

(R)-1-(H-Imidazo[1,5-a]pyridin-3-yl)-2-(7-methyl-1H-indazol-5-yl)ethanamine

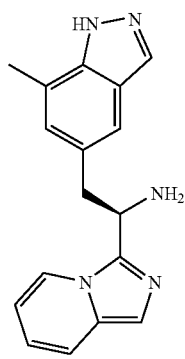

Benzyl 1-(H-imidazo[1,5-a]pyridin-3-yl)-2-(7-methyl-1H-indazol-5-yl)ethylcarbamate (50 mg, 0.11 mmol) was dissolved in methylene chloride (1.0 mL) and cooled to 0° C. Iodotrimethylsilane (67 µL, 4.0 equiv) was added and the reaction mixture allowed to warm to room temperature. After stirring for 1 h, triethylamine (57 µL, 3.0 equiv) was added to the reaction mixture and stirring continued for 30 min. The reaction was diluted with methylene chloride, washed with water (2×), brine (2×), dried over sodium sulfate, and concentrated to afford 26.0 mg (66%) which was used without purification. Mass spec.: 292.3 (MH)+.

EXAMPLE 6

(R)-N-(1-(H-Imidazo[1,5-a]pyridin-3-yl)-2-(7-methyl-1H-indazol-5-yl)ethyl)-4-(2-oxo-1,2-dihydro-quinazolin-3(4H)-yl)piperidine-1-carboxamide

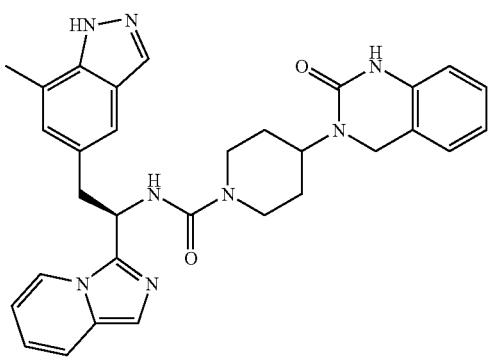

A stirred solution of 1-(H-imidazo[1,5-a]pyridin-3-yl)-2-(7-methyl-1H-indazol-5-yl)ethanamine (38.0 mg, 0.12 mmol) in dimethylformamide (1.0 mL) at 0° C. was treated with carbonyl diimidazole (21.0 mg, 1.1 equiv). The reaction was stirred for 5 min at 0° C., warmed to room temperature, stirred for 10 min, and treated with 3-(piperidin-4-yl)-3,4-dihydroquinazolin-2(1H)-one (29.8 mg, 1.1 equiv). The mixture was stirred at room temperature overnight. The solvent was evaporated and the residue purified by column chromatography to afford 29.4 mg (45%). $^1$H-NMR (CD$_3$OD, 500 MHz) δ 1.35-1.60 (m, 4H), 2.50 (s, 3H), 2.72-2.86 (m, 2H), 3.44-3.56 (m, 2H), 4.10 (s, 2H), 4.17 (dd, J=15.0, 13.1, 1H), 4.30-4.42 (m, 1H), 5.72 (dd, J=7.6, 7.3, 1H), 7.01 (s, 1H), 7.10-7.20 (m, 2H), 7.42 (s, 1H), 7.50 (d, J=9.5, 1H), 7.96 (s, 1H), 8.13 (d, J=7.3, 1H). Mass spec.: δ 549.68 (MH)$^+$.

What is claimed is:

1. A process for synthesizing a compound of Formula XIV, XV, or XVI

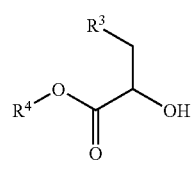
XIV

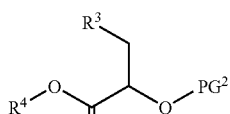
XV

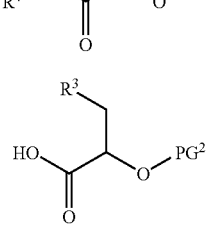
XVI wherein
$R^3$ is 7-methyl-1H-indazol-5-yl;
$R^4$ is C$_{1-6}$alkyl or benzyl; and
PG$^2$ is methoxymethyl ether, benzyloxymethyl ether, benzyl or tri-C$_{1-6}$alkylsilyl;

comprising
(a) hydrolyzing a compound of Formula XI

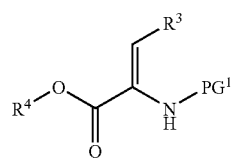
XI wherein $R^4$ is C$_{1-6}$alkyl or benzyl;
PG$^1$ is BOC, CBZ or FMOC; and
$R^3$ is 2,6-dimethylanilin-3-yl to form a compound of Formula XIII

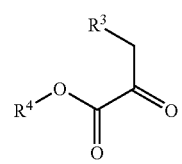
XIII (b) reducing said compound of Formula XIII to a compound of Formula XIV

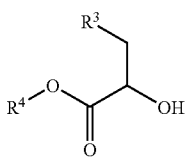
XIV (c) protecting the hydroxy moiety of compound XIV with PG$^2$
wherein PG$^2$ is methoxymethyl ether, benzyloxymethyl ether, benzyl or tri-C$_{1-6}$alkylsilyl;
to form a compound of Formula XV; and

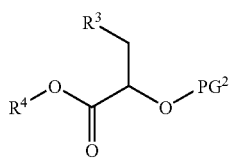
XV (d) hydrolyzing $R^4$ to form a compound of Formula XVI.

* * * * *

UNITED STATES PATENT AND TRADEMARK OFFICE
CERTIFICATE OF CORRECTION

PATENT NO. : 7,449,586 B2 Page 1 of 1
APPLICATION NO. : 11/291670
DATED : November 11, 2008
INVENTOR(S) : Prasad V. Chaturvedula et al.

It is certified that error appears in the above-identified patent and that said Letters Patent is hereby corrected as shown below:

On Title Page

Item [75], Inventors, should read

-- Prasad V. Chaturvedula
Xiaojun Han
Xiang-Jun J. Jiang --

Signed and Sealed this

Third Day of February, 2009

JOHN DOLL
*Acting Director of the United States Patent and Trademark Office*